United States Patent [19]
Cunningham et al.

[11] Patent Number: 6,096,794
[45] Date of Patent: Aug. 1, 2000

[54] QUINOLINIUM DYES AND BORATES IN PHOTOPOLYMERIZABLE COMPOSITIONS

[75] Inventors: Allan Francis Cunningham, Mount Kisco, N.Y.; Martin Kunz, Efringen-Kirchen, Germany

[73] Assignee: Ciba Specialty Chemicals Corporation, Tarrytown, N.Y.

[21] Appl. No.: 09/179,170

[22] Filed: Oct. 26, 1998

[30] Foreign Application Priority Data

Nov. 3, 1997 [EP] European Pat. Off. .............. 97810820

[51] Int. Cl.$^7$ ................ C08F 4/00; C08F 2/50; C07D 215/00; C07D 241/36
[52] U.S. Cl. .................. 522/12; 522/2; 522/15; 522/16; 522/25; 522/26; 522/28; 522/29; 522/33; 522/48; 522/63; 522/66; 522/74; 522/75; 522/78; 522/170; 522/181; 522/182; 430/270.1; 430/281.1; 430/269; 544/349; 546/152; 546/153
[58] Field of Search ............... 522/2, 7, 12, 16, 522/26, 29, 63, 66, 33, 15, 25, 28, 74, 75, 78, 170, 181, 182, 48; 430/270.1, 281.1, 269; 544/349; 546/152, 153

[56] References Cited

U.S. PATENT DOCUMENTS

| 5,807,905 | 9/1998 | Cunningham et al. | .................. 522/25 |
| 5,912,257 | 6/1999 | Prasad et al. | .............................. 522/6 |

FOREIGN PATENT DOCUMENTS

| 0 408 322 | 1/1991 | European Pat. Off. . |
| 0 441 232 | 8/1991 | European Pat. Off. . |
| 0 498 194 | 8/1992 | European Pat. Off. . |
| 0555058 | 8/1993 | European Pat. Off. . |
| 0 690 074 | 1/1996 | European Pat. Off. . |
| 2 850 585 | 2/1983 | Germany . |
| 2083832 | 3/1982 | United Kingdom . |
| 2307474 | 5/1997 | United Kingdom . |
| 97/42227 | 11/1997 | WIPO . |
| 98/52952 | 11/1998 | WIPO . |

OTHER PUBLICATIONS

Chemical Abstracts vol. 58, col. 11391.
J. Am. Chem. Soc. vol. 113(6), pp. 2155–2163, 1991.
Ann. vol. 660, pp. 23–33, 1962.
Yagci et al., Macromol. Symp. vol. 85, pp. 115–127, (1994).
A. Sarker et al., "Visible light photopolymerization employing 2,4–diiodo6–butoxy–3–fluorone and tetraorganylborate salts as photoinitiators"pp. 2817–2814.
American Chemicals Society, Macromolecules 1996, vol. 29, No. 25, 1996, pp. 8274–8276 Polykarpov et al, "Tetramethylammonium Tetraorganylborates . . . Acrylates".

Chem. Ber. 102, 1969 pp.3508–3524, Tochtermann et al "Zur Bildung und Spaltung . . . Tiiphenylboran".

Primary Examiner—Susan W. Berman
Attorney, Agent, or Firm—Luther A. R. Hall; Tyler A. Stevenson

[57] ABSTRACT

Dye compounds of the formula

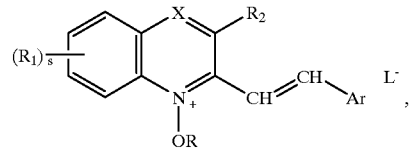

(I)

wherein

X is for example CH, C—CH$_3$ or $^+$NOR L$^-$; R is inter alia C$_1$–C$_6$alkyl; R$_1$ is for example C$_1$–C$_8$alkoxy or C$_1$–C$_{12}$alkyl; s is 0 to 4; R$_2$ is for example hydrogen; Ar is for example a group

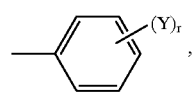

(A)

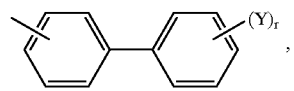

(B)

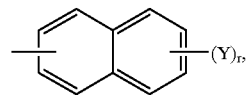

(D)

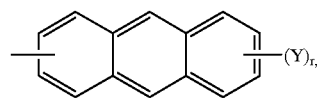

(E)

Y inter alia is C$_1$–C$_6$alkyl or C$_1$–C$_6$alkoxy; r in the formula (A) is 0 to 5, in the formulae (B) and (E) is 0 to 9 and in the formula (D) is 0 to 7; and L is an anion;

in combination with an electron donor compound, especially a borate compound, are suitable as photoinitiators for the photopolymerization of radically polymerizable compositions.

21 Claims, No Drawings

QUINOLINIUM DYES AND BORATES IN PHOTOPOLYMERIZABLE COMPOSITIONS

This invention relates to new dyes and new borates useful as photoinitiators, a photoinitiator system and a polymerisable composition, comprising the new dyes.

For free radical polymerisation of an olefinically unsaturated compound one method is to irradiate a composition containing it and a photoinitiator with electromagnetic radiation such as visible or ultraviolet light, the photoinitiator generating free radicals when so irradiated. It has now been found that photoinitiated compositions containing certain styryl-substituted heterocycles provide rapid photopolymerisation and are also bleachable by electromagnetic radiation, so that they can cause little or no discoloration of the resulting polymer and therefore can be employed in the polymerization of thick layers. Further, these new dyes are especially suitable for the photopolymerization initiated by visible lasers (e.g. argon ion laser, frequency doubled Nd/YAG).

Styryl-substituted heterocycles are for example disclosed in EP 441232 and especially in EP 498194, as well as in PCT Patent Application number EP 97/02058. Further compounds of that kind are disclosed by W. Schnabel in Macromolecular Engineering, edited by M. K. Mishra et al, Plenum Press.

It has now surprisingly been found, that some O-alkylated aromatic nitrogen-heterocycle amine oxides with specific substitutions are especially suitable as electron acceptors in photo-polymerizable compositions.

Subject of the invention therefore are photoinitiator systems comprising
(a) at least one compound of the formula I

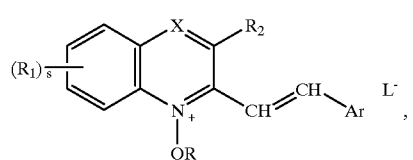
(I)

wherein
X is CH, C—CH$_3$, C—Cl, C—O—C$_1$–C$_8$alkyl or $^+$NOR L$^-$;
R is C$_1$–C$_6$alkyl, benzyl, CH$_2$COOR$_3$ or a group

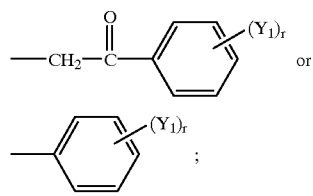
or $R_1$ is C$_1$–C$_8$alkoxy, C$_1$–C$_{12}$alkyl, halogen, NO$_2$, benzyloxy or phenyloxy, wherein the phenylring in the benzyloxy or phenyloxy group is unsubstituted or substituted by C$_1$–C$_{12}$alkyl, C$_1$–C$_6$alkoxy, halogen or CF$_3$;
s is 0 to 4;
$R_2$ is hydrogen, C$_1$–C$_8$alkoxy, C$_1$–C$_{12}$alkyl, benzyloxy or phenyloxy, wherein the phenylring in the benzyloxy or phenyloxy group is unsubstituted or substituted by C$_1$–C$_{12}$alkyl, C$_1$–C$_6$alkoxy, halogen or CF$_3$;
$R_3$ is hydrogen, C$_1$–C$_{12}$alkyl or benzyl;
Ar is a group selected from (A), (B), (C), (D), (E), (F), (G), (H), (J), (K) or (L)

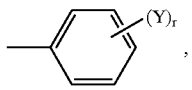
(A)

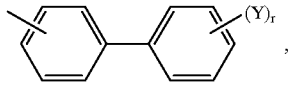
(B)

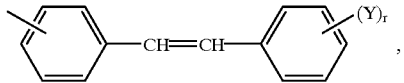
(C)

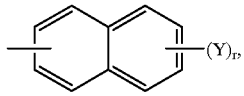
(D)

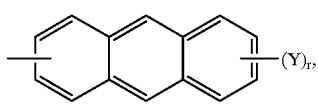
(E)

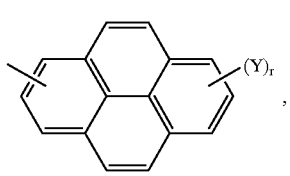
(F)

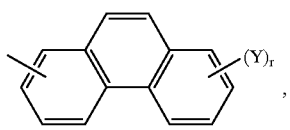
(G)

(H)

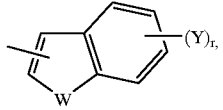
(J)

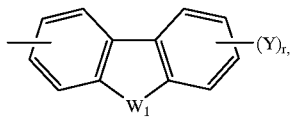
(K)

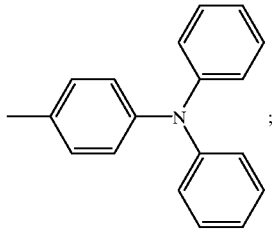
(L)

Y is unsubstituted or C$_1$–C$_6$alkoxy-substituted C$_1$–C$_6$alkyl, or Y is C$_1$–C$_6$alkoxy, halogen, CF$_3$, NO$_2$, CF$_3$O, benzyloxy or phenyloxy, wherein the phenylring in the benzyloxy or phenyloxy group is unsubstituted or substituted by $C_1$–$C_{12}$alkyl, $C_1$–$C_6$alkoxy, halogen or $CF_3$ or, if r is two or more and two Y are alkoxy these alkoxy groups may form a dioxolane or dioxane fused to the aryl of the arylstyryl residue;

$Y_1$ is unsubstituted or $C_1$–$C_6$alkoxy-substituted $C_1$–$C_6$alkyl, or $Y_1$ is $C_1$–$C_6$alkoxy, halogen, $CF_3$, $NO_2$, $CF_3O$, benzyloxy or phenyloxy, wherein the phenylring in the benzyloxy or phenyloxy group is unsubstituted or substituted by $C_1$–$C_{12}$alkyl, $C_1$–$C_6$alkoxy, halogen or $CF_3$;

W is O, S or $CH_2$;

$W_1$ is O, S, $C(R_4)_2$ or CO;

$R_4$ is hydrogen, $C_1$–$C_8$alkoxy, $C_1$–$C_{12}$alkyl, benzyloxy or phenyloxy, wherein the phenylring in the benzyloxy or phenyloxy group is unsubstituted or substituted by $C_1$–$C_{12}$alkyl or $C_1$–$C_6$alkoxy;

r in the formula (A) and the groups

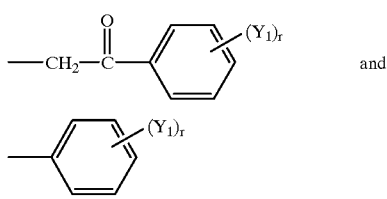

and is 0 to 5, in the formulae (B), (C), (E), (F) and (G) is 0 to 9, in the formula (D) is 0 to 7, in the formula (H) is 0 to 3, in the formula (J) is 0 to 5 and in the formula (K) is 0 to 7; with the proviso, that, if Ar is a group (A), R is $C_1$–$C_6$alkyl, benzyl, $CH_2COOR_3$ or a group

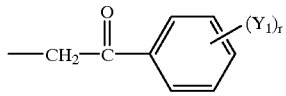

and X is not $^+$NOR L$^-$, r is 2 to 5; and

L is an anion; and optionally (b) at least one electron donor compound.

$(R_1)_s$ in the context of this application means "s" independently defined "$R_1$" substitutents, not exclusively "s" identical "$R_1$"substitutents. The same applies for $(Y)_r$ and $(Y_1)_r$, namely "r" independently defined "Y" or "$Y_1$" substitutents, not exclusively "r" identical "Y" or "$Y_1$" substituents.

"L" in the formula I is any anion. For example a tosylate, $BF_4^-$, $AsF_6^-$, $SbF_6^-$, $PF_6^{-31}$, a halogenide, perchlorate etc. It may also be a borate anion, for example one as described later on in this context according to the formulae II, III or X (wherein in the formulae II, III and X the corresponding cation "G$^+$" has to be omitted).

The invention in a further aspect provides per se, the —O-alkylated amine oxide salts generally, such salts having any anion. Therefore, the invention also pertains to compounds of the formula I as defined above.

The invention further provides a method of making the oxide cation by the steps:

(1) providing an aromatic nitrogen-heterocycle having a methylene group in one or more of the 2-, 4- and 6-positions relative to a ring nitrogen;

(2) oxidising the relevant ring nitrogen to amine oxide, for example by the action of a peroxide, e.g. peracetic acid;

(3) reacting the amine oxide with an aromatic aldehyde optionally substituted 1 to 5 times, suitably catalysed by alkali, e.g. methanolic potassium hydroxide;

(4) alkylating the product of (3) by the action of an alkylating agent such as, for example, methyl tolyl-4-sulphonate to give the oxide cation as the salt of the anion of the alkylating agent.

If the salt of another anion, e.g. a borate (as described below), is required, the method includes the further step of (5) reacting the salt with a salt of the required anion, e.g. the borate salt, suitably an (alkyl) ammonium salt, an alkaline metal salt or magnesium salt.

The reaction conditions for these reactions are generally known to the worker skilled in the art.

Suitable electron donor compounds (b) in the photoinitiator system according to the invention, for example are borates, thiols, amines, organotin compounds, phosphines, arsines, sulfinates, carboxylates or aluminates.

Preferred electron donor compounds are borates, for example those of the formulae II, IIa, III and X (described below), such as for example triphenyl butyl borate. Further suitable electron donor compounds are thiols, amines, for example triethanolamine, N-phenylglycine or (2,5-dimethyl)-1-thia-3,4-diazole, organotin compounds, for example benzyltrimethylstannane, phosphines, arsines, for example triphenylphosphine or triphenylarsine, as described for example in JP-A Hei 6 263809, sulfinates, for example sodium p-toluenesulfinate, or carboxylates, for example ascorbic acid. Coinitiators of this kind are described, for example, in Chemistry & Technology of UV & EB Formulation for Coatings, Inks & Paints, Vol.3, page 344–348 (London, 1991). Suitable aluminates are for example described in U.S. Pat. No. 5,532,373. Other electron donors are peroxides as for example described in U.S. Pat. No. 5,599,652.

For example the photoinitiator system comprises an O-alkylated aromatic nitrogen-heterocycle amine oxide salt and an electron donor compound, such as, for example a tetrahydrocarbylborate (THB), preferably of the formula II, IIa, III or X, as decribed below.

Said electron donor compound if anionic (i.e. borate, aluminate) may be a component of the amine oxide salt or may be a seperate species. A combination of several electron donor compounds may also be employed. Thus, the photoinitiator system according to the invention comprises both the borate salt of the amine oxide cation with or without additional electron donor compounds (b) as well as the combination of another type of amine oxide cation salt (e.g. anion=$PF_6^-$, tosylate$^-$, halogen$^-$, etc.) with any borate salt (e.g. cation=tetraalkylammonium, phosphonium, sulfonium, iodonium, etc.). Wherein the "cation" and "anion" are any positive or negative ionic species.

If an electron donor compound is comprised in the formula I in the form of the anion (=L), the addition of a seperate electron donor component (b) in the photoinitiator system according to the invention is not unequivocally necessary.

If a THB anion is present, it preferably contains hydrocarbon radicals of more than one type, for example some aromatic and some aliphatic, so that when liberated as a free radical it readily dissociates into a hydrocarbon free radical and a tri-hydrocarbyl boron.

The THB anion preferably has 3 aromatic radicals and 1 aliphatic radical linked to boron. Suitably the aromatic radicals are phenyl optionally carrying one or more non-reactive substituents such as halogen, alkyl or alkoxy. Suitably the aliphatic radical contains 2–8 carbon atoms, is saturated and may be branched or cyclic.

Suitable borate compounds, either as electron donor (b) or as anion "L" for the dye of the formula I (in this case, without the defined cation G) for the present photoinitiator systems are especially compounds of the formula II or IIa

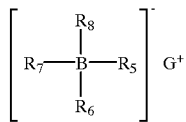
(II)

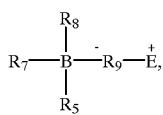
(IIa)

wherein $R_5$, $R_6$, $R_7$ and $R_8$ independently of one another are phenyl or another aromatic hydrocarbon, with or without any heteroatoms, which aromatic radicals are unsubstituted or are substituted 1–5 times by unsubstituted or halogen-, $OR_{10}$— or $R_{11}R_{12}N$-substituted $C_1$–$C_{20}$alkyl, $C_2$–$C_{20}$alkyl which is interrupted by one or more radicals O, $S(O)_p$ or $NR_{13}$, or the aromatic radicals are substituted by $OR_{10}$, $R_{10}S(O)_p$, $R_{10}S(O)_2O$, $R_{11}R_{12}N$, $R_{10}OC(O)$, $R_{11}R_{12}NC(O)$, $R_{14}C(O)$, $R_{14}R_{15}R_{16}Si$, $R_{14}R_{15}R_{16}Sn$, halogen, CN, $R_{14}R_{15}P(O)_q$, CN and/or

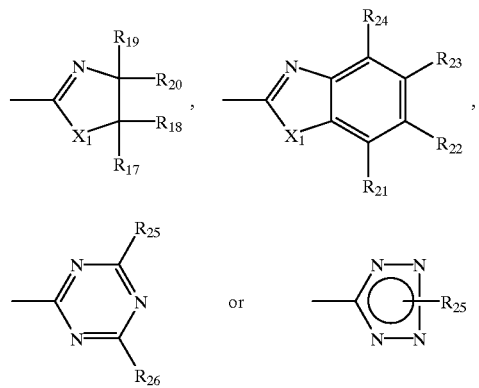

or the radicals $R_5$ and $R_6$ form bridges to produce structures of the formula IV, IVa or IVb

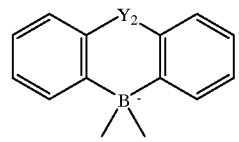
(IV)

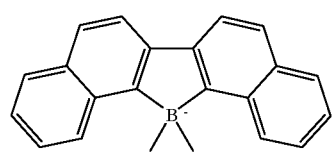
(IVa)

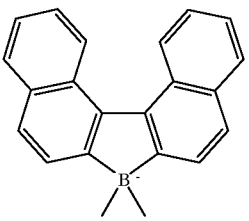
(IVb)

whose aromatic rings are unsubstituted or are substituted by $C_1$–$C_{20}$alkyl, by $C_2$–$C_{20}$alkyl which is interrupted by one or more radicals O, $S(O)_p$ or $NR_{13}$, or the aromatic rings are substituted by $OR_{10}$, $R_{10}S(O)_p$, $R_{10}S(O)_2O$, $R_{11}R_{12}N$, $R_{10}OC(O)$, $R_{11}R_{12}NC(O)$, $R_{14}C(O)$, $R_{14}R_{15}R_{16}Si$, halogen, CN, $R_{14}R_{15}P(O)_q$ and/or $R_{14}R_{15}R_{16}Sn$, or $R_5$, $R_6$, $R_7$ and $R_8$ independently of one another are $R_{14}R_{15}R_{16}Si$, or $R_5$, $R_6$, $R_7$ and $R_8$ independently of one another are $C_1$–$C_{20}$alkyl, $C_2$–$C_{20}$alkyl which is interrupted by one or more radicals O, $S(O)_p$ or $NR_{13}$, or is $C_3$–$C_{12}$cycloalkyl, $C_2$–$C_8$alkenyl, phenyl-$C_1$–$C_6$alkyl or naphthyl-$C_1$–$C_3$alkyl, where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or are substituted by $OR_{10}$, $R_{10}S(O)_p$, $R_{10}OS(O)_2O$, $R_{11}R_{12}N$, $R_{10}OC(O)$, $R_{11}R_{12}NC(O)$, $R_{14}C(O)$, $R_{14}R_{15}R_{16}Si$, $R_{14}R_{15}R_{16}Sn$, halogen, $R_{14}R_{15}P(O)_q$, and/or CN;

$R_9$ is a divalent aromatic hydrocarbon radical which is unsubstituted or is substituted by $C_1$–$C_6$alkyl, $OR_{10}$, $R_{10}S(O)_p$, $R_{10}S(O)_2O$, $R_{11}R_{12}N$, $R_{10}OC(O)$, $R_{11}R_{12}NC(O)$, $R_{14}C(O)$, $R_{14}R_{15}R_{16}Si$, CN or halogen, or $R_9$ is phenyl-$C_1$–$C_6$alkylene;

E is $R_{27}R_{28}R_{29}P$, $R_{10}R_{11}R_{12}N$ or $R_{10}R_{30}S$;

$R_{27}$, $R_{28}$ and $R_{29}$ independently of one another are $C_1$–$C_{12}$alkyl, $C_2$–$C_{12}$alkenyl or $C_3$–$C_{12}$cycloalkyl, where the radicals $C_1$–$C_{12}$alkyl, $C_2$–$C_{12}$alkenyl and $C_3$–$C_{12}$cycloalkyl are unsubstituted or are substituted by $R_{10}OCO$ or CN, or $R_{27}$, $R_{28}$ and $R_{29}$ are unsubstituted or mono- to penta-$C_1$–$C_6$alkyl-, —$C_1$–$C_{12}$alkoxy- or -halogen-substituted phenyl-$C_1$–$C_6$alkyl or are unsubstituted or mono- to penta-$C_1$–$C_6$alkyl-, —$C_1$–$C_{12}$alkoxy- or -halogen-substituted phenyl;

$Y_2$ is $(CH_2)_x$, CH=CH, C(O), $NR_{13}$, O, $S(O)_p$ —$CR_{31}R_{32}$—;

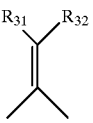 or 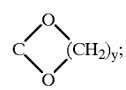

x is 0, 1, 2 or 3;
y is 2 or 3;
p is 0, 1 or 2;
q is 0 or 1;
$R_{10}$ and $R_{30}$ independently of one another are unsubstituted or halogen-substituted $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;
$R_{11}$, and $R_{12}$ independently of one another are hydrogen, unsubstituted or $C_1$–$C_{12}$alkoxy-, halogen-, OH—, $COOR_{10}$— or CN-substituted $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen, or $R_{11}$ and $R_{12}$, together with the N atom to which they are attached, form a 5- or 6-membered ring which may additionally contain O or S atoms;

$R_{13}$ is hydrogen, $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;

$R_{14}$, $R_{15}$ and $R_{16}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;

$R_{17}$, $R_{18}$, $R_{19}$ and $R_{20}$ independently of one another are hydrogen, unsubstituted or $C_1$–$C_{12}$alkoxy-substituted $C_1$–$C_{12}$alkyl, unsubstituted or mono- to penta-$C_1$–$C_6$alkyl-, —$C_1$–$C_{12}$alkoxy- or -halogen-substituted phenyl-$C_1$–$C_6$alkyl or are unsubstituted or mono- to penta-$C_1$–$C_6$alkyl-, —$C_1$–$C_{12}$alkoxy- or -halogen-substituted phenyl, or any two of the radicals $R_{17}$, $R_{18}$, $R_{19}$ and $R_{20}$ together form an aromatic ring to which further aromatic rings may be fused;

$R_{21}$, $R_{22}$, $R_{23}$, $R_{24}$, $R_{25}$ and $R_{26}$ independently of one another are hydrogen, unsubstituted or $C_1$–$C_{12}$alkoxy-, OH— or halogen-substituted $C_1$–$C_{12}$alkyl or are unsubstituted or $C_1$–$C_{12}$alkyl-, $C_1$–$C_{12}$alkoxy-, OH— or halogen-substituted phenyl;

$R_{31}$ and $R_{32}$ are $C_1$–$C_6$alkyl or phenyl, or $R_{31}$ and $R_{32}$, together with the C atom to which they are attached, form a 5- or 6-membered ring;

$X_1$ is N, S or O; and

G is a radical which is able for form positive ions.

Specific examples for compounds of the formula II and IIa, as well as their preparation are published in GB 2307474, GB 2307473 and GB 2307472, which technology hereby is incorporated by reference.

Examples for compounds of the formula IIa are

Methyl 4-[(phenyl)(methyl)sulfonio]phenyl dimesityl borate (compound of the formula IIa, in which $R_8$ and $R_5$=mesityl, $R_7$=methyl, $R_9$=phenylene and E=

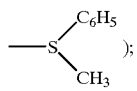

Methyl 1-trimethylammonionaphthyl dimesityl borate (compound of the formula IIa, in which $R_8$ and $R_5$=mesityl, $R_7$=methyl, $R_9$=naphthylene and E=N(CH$_3$)$_3$);

Methyl 1-benzyldimethylammonionaphthyl dimesityl borate (compound of formula IIa, in which $R_8$ and $R_5$=mesityl, $R_7$=methyl, $R_9$=naphthylene and E=N(CH$_3$)$_2$(CH$_2$C$_6$H$_5$));

More examples for compounds of the formulae II and IIa are disclosed in U.S. Pat. Nos. 5,176,984, 5,151,520, 5,100,755, 5,057,393, 5,100,755, 4,954,414 and 4,772,530, EP 0710887, U.S. Pat. Nos. 3,567,453, 4,343,891, EP 0109772, EP 0109773, JP Kokai Hei 5-255347, JP Kokai Hei 2-108055, U.S. Pat. No. 5,168,032, EP 0726497, JP Kokai Hei 4-146905, JP Kokai Hei 4-261405 and JP Kokai Hei 5-61247.

Specific examples for suitable borate anions are also triphenyl-s-butyl borate, triphenyl-neopentyl borate, triphenyl-hexyl borate, triphenyl-n-butyl borate, triphenyl-methyl borate, triphenyl-heptyl borate, triphenyl-ethyl borate, triphenyl-benzyl borate, tris(p-methoxyphenyl)-butyl borate, tris(p-tert-butylphenyl)-butyl borate, triphenyl-benzyl borate, triphenyl-(p-fluorobenzyl) borate, triphenyl-(p-methylbenzyl) borate, triphenyl-(o-methylbenzyl) borate, tris(p-fluorophenyl)-butyl borate, tris(p-methoxyphenyl)-butyl borate, tris(p-methoxyphenyl)-hexyl borate, tris(p-methoxyphenyl)-octyl borate, triphenyl-octyl borate, tributyl-(triphenylsilyl) borate, tributyl-(di-methyl-phenylsilyl) borate, diphenyl-octyl-(dibutyl-phenylsilyl) borate, dimethyl-phenyl-(trimethylsilyl) borate or diphenyl-butyl-(dimethyl-phenylsilyl) borate.

Further borate compounds which are suitable either as anion L for the dye compounds according tio the present invention or as component b) in the photoinitiator system according to the present invention are given in the following, and in particular are triaryl-cycloalkyl borates. Specific examples are:

Tetramethylammonium tris(3-fluorophenyl)-cyclohexyl borate (m.p.>230° C.), tetramethylammonium tris(3-trifluoromethylphenyl)-cyclohexyl borate (m.p.90–92° C.), tetramethylammonium triphenyl-cyclohexyl borate (m.p.>230° C.), tetramethylammonium tris(2-methylphenyl)-cyclohexyl borate (m.p.>200° C.), tetramethylammonium tris(3-fluorophenyl)-bicyclo[2.2.1]heptyl borate (m.p.188–189° C.), tetramethylammonium tris(3-trifluoromethylphenyl)-bicyclo[2.2.1]heptyl borate (m.p.70–72° C.), tetramethylammonium triphenyl-bicyclo [2.2.1]heptyl borate (m.p.>230° C.), tetramethylammonium hexyl tris(halotolyl)borate, tetramethylammonium tris-(3-fluorophenyl)-cycloheptyl borate (m.p. 229–231° C.), tetramethylammonium tris(3-trifluoromethylphenyl)-cycloheptyl borate (m.p. 77–80° C.), tetramethylammonium triphenyl-cycloheptyl borate (m.p.>230° C.), tetramethylammonium tris(3-fluorophenyl)-cyclooctyl borate (m.p.>230° C.), tetramethylammonium tris(3-trifluoromethylphenyl)-cyclooctyl borate (m.p. 83–87° C.), tetramethylammonium triphenyl-cyclooctyl borate (m.p.>230° C.), tetramethylammonium bis(3-fluorophenyl)-bis(n-hexyl) borate (resin), tetramethylammonium tris(4-methoxyphenyl)-n-hexyl borate (m.p. 129–130° C.), tetramethylammonium tris(2-methylphenyl)-n-hexyl borate (m.p. 165–168° C.), tetramethylammonium triphenyl-n-hexyl borate (m.p. 220–225° C.), tetramethylammonium tris(4-fluorophenyl)-n-hexyl borate (m.p. 120–125° C.), tetramethylammonium tris(4-trimethylsilylphenyl)-n-hexyl borate (m.p. 175–177° C.), tetramethylammonium tris(biphenylyl)-n-hexyl borate (m.p. 200–202° C.), tetramethylammonium tris(2-naphthyl)-n-hexyl borate (m.p. 180–181° C.), tetramethylammonium tris(3-methoxyphenyl)-n-hexyl borate, tetrabutylammonium tris(3-fluorophenyl)-benzyl borate (m.p. 90–101° C.).

These borates are prepared by first synthesizing the corresponding dialkoxy alkyl- or cycloalkyl-boronates and subsequently transforming the boronates into the borate by reacting it with a Grignard reagent of corresponding aryl bromide. Other methods of borate synthesis are described in the aforementioned patents and patent applications.

Some cycloalkyl triaryl borate compounds are known: tetramethylammonium cyclopentyl-triphenyl borate (disclosed in Macromolecules 1996, 29, 8274–8276 or Journal of Polymer Science: Part A: Polymer Chemistry, Vol. 34, 2817–24 (1996)); sulfonium cyclohexyl-triphenyl borate, sulfonium cyclohexyl tris(p-methoxyphenyl) borate; sulfonium cyclohexyl tris(p-fluorophenyl borate (disclosed in EP 690074) and

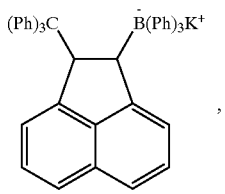

wherein "Ph" means
phenyl (disclosed in Chem. Ber. 102, 3508–24 (1969)).

Other suitable and preferred cycloalkyl-triaryl borate compounds are those of the formula X

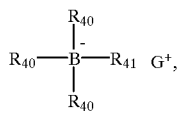
(X)

wherein $R_{40}$ is phenyl which is unsubstituted or substituted 1–5 times by halogen, $C_1$–$C_4$alkoxy, $C_1$–$C_{20}$alkyl or $C_1$–$C_{20}$haloalkyl;

$R_{41}$ is $C_3$–$C_{12}$cycloalkyl, which may be condensed with one or more aromatic rings; and G is a radical which is able to form positive ions, preferably a dye compound of formula I.

Compounds of formula X with the following provisions are new and also a subject of the invention
provided that
(a) if $R_{41}$ is $C_3$–$C_6$cycloalkyl, $R_{40}$ is no unsubstituted phenyl or phenyl mono-substituted in the para-position; and
(b) if $R_{40}$ is unsubstituted phenyl, $R_{41}$ is no substituted 1-acenaphthenyl.

Preferably $R_{40}$ is phenyl which is substituted in the 3-position by halogen, $C_1$–$C_4$alkoxy, $C_1$–$C_{20}$alkyl or $C_1$–$C_{20}$haloalkyl, particularly 3-fluorophenyl or 3-trifluoromethylphenyl.

Interesting are compounds of formula X, wherein $R_{41}$ is cyclohexyl, and G is a cation, with the exception of sulfonium cations.

Preferred are cations G other than sulfonium salts as described in EP 690074.

$R_{41}$ is $C_3$–$C_{12}$cycloalkyl, for example $C_7$–$C_{12}$cycloalkyl, in particular cycloheptyl or cyclooctyl, preferably cycloheptyl.

Especially $R_{41}$ is cyclopentyl, cyclohexyl, cycloheptyl and cyclooctyl as well as bicyclo[2.2.1]-heptyl. $R_{40}$ preferably is phenyl, 2-methylphenyl, 2,4-trimethylphenyl, 3-fluorophenyl and 3-trifluoromethylphenyl. The meanings and preferences for G are as defined below.

$R_{41}$ also may be a heterocycloalkyl. Starting materials for these compounds are for example oxo-cycloalkylboronates or sulfo-cycloalkylboronates, e.g.

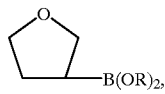 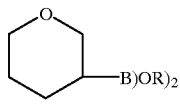 or

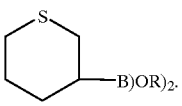

Specific examples of compounds of formula X, as well as their preparation, are given in examples 13–29 below.

Other suitable borate compounds for the present photoinitiator systems either as electron donor (b) or as anion for the dye of the fomula I (in this case, without the defined cation G) are compounds of the formula III

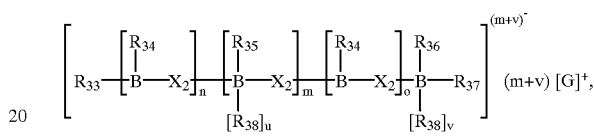
(III)

wherein n, m and o are each a number from 0 to 50, but are not simultaneously 0;

u and v are 0 or 1, and at least one of the indices u and v is 1;

$R_{33}$, $R_{34}$, $R_{35}$, $R_{36}$ and $R_{37}$ independently of one another are phenyl or another aromatic hydrocarbon, which radicals are unsubstituted or are substituted by unsubstituted or halo-, $OR_{10}$— and /or $NR_{11}R_{12}$-substituted $C_1$–$C_6$alkyl, or are substituted by $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, $P(O)_qR_{14}R_{15}$, CN or halogen;

p is 0, 1 or 2;

q is 0 or 1;

$R_{38}$ is $C_1$–$C_{12}$alkyl, $C_3$–$C_{12}$cycloalkyl, $C_2$–$C_8$alkenyl, phenyl-$C_1$–$C_6$alkyl or naphthyl-$C_1$–$C_3$alkyl, the radicals $C_1$–$C_{12}$alkyl, $C_3$–$C_{12}$cycloalkyl, $C_2$–$C_8$alkenyl, phenyl-$C_1$–$C_6$alkyl or naphthyl being unsubstituted or substituted by $OR_{10}$, $S(O)_pR_{10}$, $S(O)_2R_{10}$, $NR_{11}R_{12}$, $C(O)OR_{10}$, $C(O)NR_{11}R_{12}$, $C(O)R_{14}$,

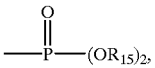

$SiR_{14}R_{15}R_{16}$, $BR_{39}R_{40}$, CN or halogen, or $R_{38}$ is phenyl or another aromatic hydrocarbon radical, which radicals are unsubstituted or substituted by $C_1$–$C_6$alkyl, $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, CN or halogen, at least one of the radicals $R_{33}$, $R_{34}$, $R_{35}$, $R_{36}$ and $R_{37}$ being a phenyl radical which is substituted ortho to the bond to the boron atom, or being another aromatic hydrocarbon radical which is sterically hindered ortho to the boron atom;

$R_{10}$, $R_{11}$, $R_{12}$, $R_{13}$, $R_{14}$, $R_{15}$, $R_{16}$ are as defined above for the formula II;

$R_{39}$ and $R_{40}$ independently of one another are as defined for $R_{10}$ or are $C_3$–$C_{12}$cycloalkyl, or together with the B atom to which they are attached, form a 5- or 6-membered ring;

$X_2$ is $C_1$–$C_{20}$alkylene which is unsubstituted or substituted by $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, CN, halogen or $P(O)_qR_{14}R_{15}$, or $X_2$ is $C_3$–$C_{12}$cycloalkylene or $C_2$–$C_8$alkenylene, each of which is unsubstituted or substituted by $OR_{10}$, $S(O)_pR_{10}$, $OS(O)_2R_{10}$, $NR_{11}R_{12}$, C(O)

OR$_{10}$, C(O)NR$_{11}$R$_{12}$, C(O)R$_{14}$, SiR$_{14}$R$_{15}$R$_{16}$, BR$_{39}$R$_{40}$, CN or halogen, or where these radicals are interrupted by one or more groups —O—, —S(O)$_p$— or —NR$_{13}$—, or X$_2$ is a divalent aromatic hydrocarbon radical which is unsubstituted or substituted by C$_1$–C$_6$alkyl, OR$_{10}$, S(O)$_p$R$_{10}$, OS(O)$_2$R$_{10}$, NR$_{11}$R$_{12}$, C(O)OR$_{10}$, C(O)NR$_{11}$R$_{12}$, C(O)R$_{14}$, SiR$_{14}$R$_{15}$R$_{16}$, BR$_{39}$R$_{40}$, CN, halogen, or X$_2$ is C$_1$–C$_{20}$alkylene which is interrupted by one or more groups —O—, —S(O)$_p$— or —NR$_{13}$—, or X$_2$ is a radical of the formula V or VI

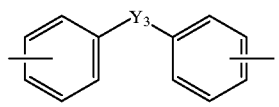
(V)

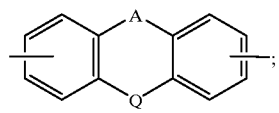
(VI)

Y$_3$ is —(CH$_2$)$_x$—, —C(O)—, —NR$_{13}$—, —O—, —S(O)$_p$—, —CR$_{31}$R$_{32}$—, —CH=CH—,

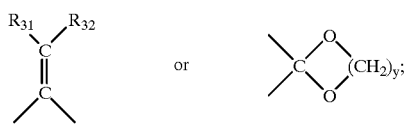

x is 0, 1, 2 or 3;

y is 2 or 3;

R$_{31}$ and R$_{32}$ are C$_1$–C$_6$alkyl or phenyl, or R$_{31}$ and R$_{32}$, together with the C atom to which they are attached, form a 5- or 6-membered ring;

A and Q independently of one another are a direct bond, —(CH$_2$)$_x$—, —CH=CH—, —C(O)—, —NR$_{13}$—, —S(O)$_p$—, —CR$_{31}$R$_{32}$—,

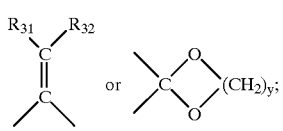

or the radicals R$_{33}$, R$_{34}$, R$_{35}$, R$_{36}$ and X$_2$ form bridges to produce radicals of the formula (VII) or (VIII)

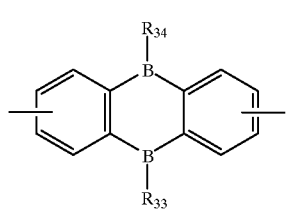
(VII)

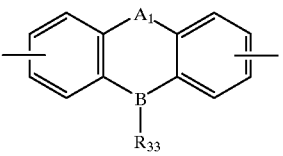
(VIII)

A$_1$ is —(CH$_2$)$_t$—, —CH=CH—, —C(O)—, —NR$_{13}$—, —O—, —S(O)$_p$—, —CR$_{31}$R$_{32}$—,

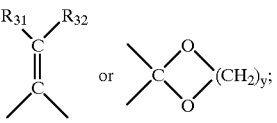

t is 0, 1 or 2;

the radicals of the formulae (V), (VI), (VII) and (VIII) being unsubstituted or being substituted on the aromatic rings by OR$_{10}$, S(O)$_p$R$_{10}$, OS(O)$_2$R$_{10}$, NR$_{11}$R$_{12}$, C(O)OR$_{10}$, C(O)NR$_{11}$R$_{12}$, C(O)R$_{14}$, SiR$_{14}$R$_{15}$R$_{16}$, BR$_{39}$R$_{40}$, CN or halogen and where additional phenyl rings may be fused to the phenyl rings of the formulae (V), (VI), (VII) and (VIII);

G is a radical which is able to form positive ions.

Examples of suitable compounds of the formula III are listed below.

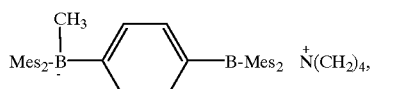

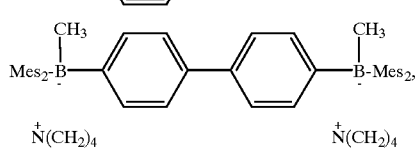

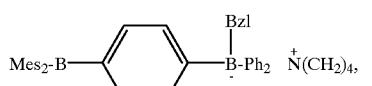

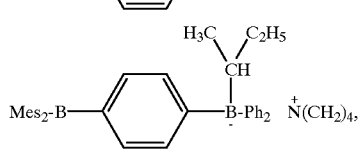

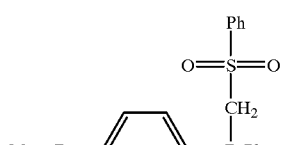

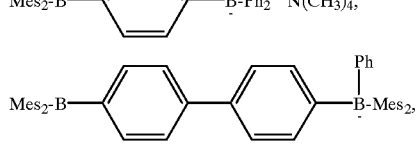

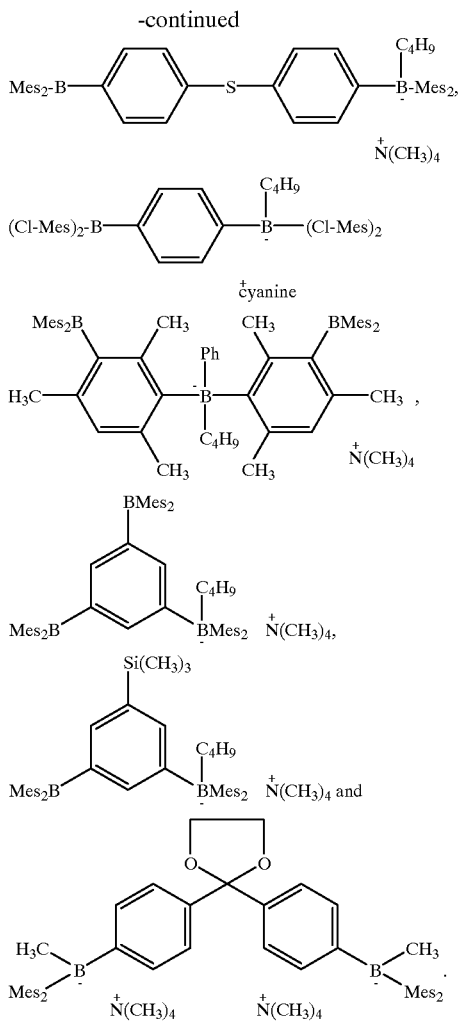

"Mes" is Mesityl, "Cl-Mes" is chloromesityl, "Bzl" is benzyl, "Ph" is phenyl, "QTX" and "cyanine" are as defined below. Further examples for compounds of the formula III, as well as their preparation are disclosed in the EP 775706.

The following explanations of definitions are applicable for all the corresponding definitions, e.g. in formulae I, II, IIa, III and X, given in the whole application:

"Aromatic hydrocarbons" as may be present in the borate compounds may, for example, contain one or more, especially 1 or 2, heteroatoms. Examples of suitable heteroatoms are N, O, P or S, preferably N or O. Examples of aromatic hydrocarbon radicals are phenyl, α- and β-naphthyl, stilbenyl, biphenyl, o-, m-, p-terphenyl, triphenylphenyl, binaphthyl, anthracyl, phenanthryl, pyrenyl, furan-2-yl or furan-3-yl, thiophen-2-yl or thiophen-3-yl, pyridin-2-yl, pyridin-3-yl or pyridin-4-yl quinolyl or isoquinolyl. If the radicals phenyl, stilbenyl, biphenyl, o-, m- or p-terphenyl, triphenylphenyl, naphthyl, binaphthyl, anthracyl, phenanthryl, pyrenyl, ferrocenyl, furanyl, thiophenyl, pyridinyl, quinolinyl or isoquinolinyl are substituted, they are so one to four times, for example one, two or three times, especially one or two times. Substituents on the phenyl ring are preferably in positions 2, or in 2,6 or 2,4,6 on the phenyl ring.

"$C_1$–$C_{20}$alkyl" is linear or branched and is, for example, $C_1$–$C_{12}$, $C_1$–$C_8$, $C_1$–$C_6$ or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl or eicosyl. $C_1$–$C_{12}$alkyl and $C_1$–$C_6$alkyl are likewise linear or branched and have, for example, the definitions indicated above up to the corresponding number of C atoms. Where $C_1$–$C_{20}$alkyl is substituted one or more times by halogen, there are, for example, 1 to 3 or 1 or 2 halogen substituents on the alkyl radical.

"$C_2$–$C_{20}$alkyl which is interrupted one or more times by —O—, —S(O)$_p$— or —NR$_{13}$-" is, for example, interrupted 1–9 times, for example 1–7 times or 1 or 2 times, by —O—, —S(O)$_p$— or —NR$_{13}$—. This produces structural units such as, for example, —CH$_2$—O—CH$_3$, —CH$_2$CH$_2$—O—CH$_2$CH$_3$, -[CH$_2$CH$_2$O]$_y$—CH$_3$, where y=1–9,— (CH$_2$CH$_2$O)$_7$CH$_2$CH$_3$, —CH$_2$—CH(CH$_3$)—O—CH$_2$—CH$_2$CH$_3$, —CH$_2$—CH(CH$_3$)—O—CH$_2$—CH$_3$, —CH$_2$SCH$_3$ or —CH$_2$—N(CH$_3$)$_2$.

"$C_3$–$C_{12}$Cycloalkyl" is, for example, cyclopropyl, cyclopentyl, cyclohexyl, cyclooctyl, cyclo-dodecyl, especially cyclopentyl and cyclohexyl, preferably cyclohexyl.

"$C_2$–$C_8$alkenyl" radicals can be mono- or polyunsaturated and are, for example, allyl, methallyl, 1,1-dimethylallyl, 1-butenyl, 3-butenyl, 2-butenyl, 1,3-pentadienyl, 5-hexenyl or 7-octenyl, especially allyl.

"Phenyl-$C_1$–$C_6$alkyl" is, for example, benzyl, phenylethyl, α-methylbenzyl, phenylpentyl, phenylhexyl or α,α-dimethylbenzyl, especially benzyl. Preference is given to phenyl-$C_1$–$C_4$alkyl, especially phenyl- $C_1$–$C_2$alkyl. Substituted phenyl-$C_1$–$C_6$alkyl is substituted one to four times, for example once, twice or three times, especially once or twice, on the phenyl ring.

"Phenyl-$C_1$–$C_6$alkylene" has two free bonds of which one is on the phenylene ring and the other in the alkylene radical.

"Substituted phenyl" is substituted one to five times, for example once, twice or three times, especially once or twice, on the phenyl ring.

"Naphthyl-$C_1$–$C_3$alkyl" is for example, naphthylmethyl, naphthylethyl, naphthylpropyl or naphthyl-1-methylethyl, especially naphthylmethyl. The alkyl unit can be in either position 1 or position 2 of the naphthyl ring system. Substituted naphthyl-$C_1$–$C_3$alkyl is substituted one to four times, for example once, twice or three times, especially once or twice, on the aromatic rings.

"$C_1$–$C_{12}$alkoxy" denotes linear or branched radicals and is, and is, for example, $C_1$–$C_8$, $C_1$–$C_6$ or $C_1$–$C_4$alkoxy. Examples are methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy, tert-butyloxy, preferably methoxy. $C_1$–$C_8$alkoxy and $C_1$–$C_6$alkoxy have the same meanings as given for $C_1$–$C_{12}$alkoxy, up to the corresponding number of C-atoms.

"Halogen" is fluorine, chlorine, bromine and iodine, especially fluorine, chlorine and bromine, preferably fluorine and chlorine.

Where R$_{11}$ and R$_{12}$, together with the N atom to which they are attached, form a 5- or 6-membered ring which may additionally contain O or S atoms, then the rings involved are, for example, saturated or unsaturated rings, for example aziridine, pyrrol, pyrrolidine, oxazole, thiazole, pyridine, 1,3-diazine, 1,2-diazine, piperidine or morpholine.

The "floating bonds" defined in formulae (B), (C), (D), (E), (F), (G), (J) and (K) are meant to be positioned at any C-atom of appropriate valence of the whole aromatic ring system.

Radicals generally suitable as a counterion "G+" to the negative borate in the formulae II, IIa, III and X are those which are able to form positive ions. Thus, "G" in formula II or IIa, as well as in formula III and X, for example, is a metal from group I of the Periodic Table in the first oxidation state, especially Na+, K+ or Li+, or G is $MgZ_1^+$ or $CaZ_1^+$ in which $Z_1$ is a halogen or $C_1$–$C_4$alkoxy, or G is an ammonium ion, sulfonium ion, iodonium ion or phosphonium ion or, for example, a dye cation, or a transition metal complex cation. Examples of the counterions "G" are alkali metals, especially lithium or sodium, quaternary ammonium compounds, for example tetra($C_1$–$C_4$alkyl)ammonium cations, dye cations or cationic transition metal coordination complex compounds. Especially preferred are ammonium, tetraalkylammonium or dye cations. Trisalkylammonium ions, for example trimethylammonium, are also suitable. Suitable phosphonium and ammonium counterions are those of the formulae $^+PR_wR_xR_yR_z$ and $^+NR_wR_xR_yR_z$, where $R_w$, $R_x$, $R_y$, $R_z$ independently of one another are hydrogen, unsubstituted or substituted alkyl, cycloalkyl, alkenyl, phenyl or arylalkyl. Substituents for these alkyl, cycloalkyl, alkenyl, phenyl or arylalkyl radicals are, for example, halide, hydroxyl, heterocycloalkyl (e.g. epoxy, aziridyl, oxetanyl, furanyl, pyrrolidinyl, pyrrolyl, thiophenyl, tetrahydrofuranyl, etc.), dialkylamino, amino, carboxyl, alkyl- and arylcarbonyl and aryloxy- and alkoxycarbonyl. The tetravalent nitrogen may also be part of a 5- or 6-membered ring, in which case this ring may in turn be fused to other ring systems. These sysems may also contain additional heteroatoms, for example S, N, O. The tetravalent nitrogen may also be part of a polycyclic ring system, for example azoniapropellane. These systems may also contain further heteroatoms, for example S, N, O.

The term "tetraalkylammonium" or "tetra($C_1$–$C_4$alkyl) ammonium" respectively, refers to compounds of the following formula: $N(C_1$–$C_4alkyl)^+_4$, where $C_1$–$C_4$alkyl can have the definitions given above up to the corresponding number of C atoms. Examples of appropriate ammonium compounds are tetramethylammonium, tetraethylammonium, tetrapropylammonium or tetrabutylammonium, especially tetramethylammonium and tetrabutylammonium. Benzyltri-($C_1$–$C_4$alkyl)ammonium is $C_6H_5$—$CH_2$—$N(C_1$–$C_4alkyl)_3^+$, where $C_1$–$C_4$alkyl can have the definitions given above up to the corresponding number of C atoms. Examples of such radicals are benzyltrimethylammonium, benzyltriethylammonium, benzyltripropylammonium and benzylbutylammonium, especially benzyltrimethylammonium and benzyltributylammonium.

Also suitable are polyammonium salts and polyphosphonium salts, especially the bis salts, in which it is possible for the same substituents to be present as described above for the "mono" compounds. Polyammonium ions can refer to a monoborate and other anions, to se-veral monoborates or to a polyborate e.g. of the formula III.

The ammonium salts and phosphonium salts may also be substituted by neutral dyes (e.g. thioxanthenenes, thioxanthones, coumarins, ketocoumarins, etc.). Such salts are obtained by the reaction of the ammonium salts and phosphonium salts, substituted by reactive groups (e.g. epoxy, amino, hydroxyl, etc.), with appropriate derivatives of neutral dyes. Corresponding examples are described in EP 224 967 (QUANTACURE QTX).

Similarly, ammonium salts and phosphonium salts can also be substituted by colourless electron acceptors (e.g. benzophenones); examples of these are

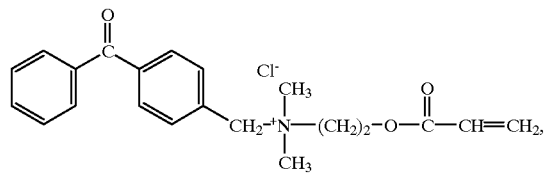

QUANTACURE ABQ

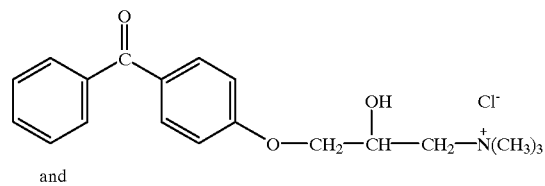

QUANTACURE BPQ and

QUANTACURE BTC

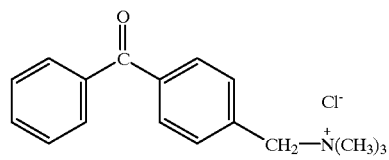

from International Bio-Synthetics.

Other quaternary ammonium compounds which are of interest are, for example, trimethylcetylammonium or cetylpyridinium compounds.

Other examples to be used as positive counterions G+ in the compounds of the formulae I, IIa, III and X include the following:

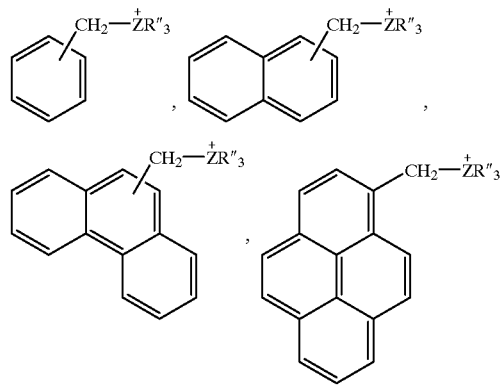

in which Z is P, N or S and R" is an alkyl or aryl radical. Also suitable are compounds such as

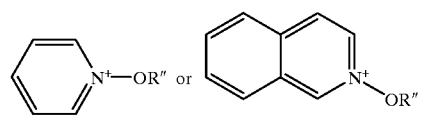

(described by Yagci et al. in J. Polym. Sci. Part A: Polymer Chem. 1992, 30, 1987 and Polymer 1993, 34 (6), 1130) or compounds such as

[Pyridinium and isoquinolinium structures with N⁺—R']

where R'=unsubstituted or substituted benzyl or phenacyl (described in JP Kokai Hei 7 70221). In these compounds, the aromatic rings in the pyridinium may also be substituted.

Other positive counterions G⁺ to the borate which can be employed are other onium ions, for example iodonium or sulfonium ions. Examples of such counterions to the borate are radicals of the formula $$R_q\text{—}S^+(R_o)(R_p)$$

as described, for example, in EP 555 058 and EP 690 074.

Also of interest as counterions are

[Structures showing Phenyl-S⁺ substituted biphenyl/terphenyl sulfonium cations with Phenyl groups, including mono-, di-cationic and polymeric forms]

Further suitable counterions for the novel borates are cations of the formula

[Isothiochromanone sulfonium structure with S⁺—R_g]

in which $R_9$ is an alkyl radical, especially ethyl, or benzyl, and where the aromatic ring can carry further substituents.

Other suitable counterions are halonium ions, especially diaryliodonium ions, as described for example in EP 334 056 and EP 562 897.

However, cations of ferrocenium salts are also suitable, as described, for example, in EP 94915 and EP 109851, for example

[Isopropylbenzene-cyclopentadienyl iron cation (ferrocenium) structure]

Other suitable "onium" cations, such as ammonium, phosphonium, sulfonium, iodonium, selonium, arsonium, tellonium and bismuthonium, are described, for example, in JP Application Hei 6 266102.

Examples of cationic transition metal complex compounds which are suitable as counterions are described in U.S. Pat. No. 4,954,414. Of particular interest are bis(2,2'-bipyridine)(4,4'-dimethyl-2,2'-bipyridine)ruthenium, tris(4, 4'-dimethyl-2,2'-bipyridine)ruthenium, tris(4,4'-dimethyl-2, 2'-bipyridine)iron, tris(2,2',2"-terpyridine)ruthenium, tris(2, 2'-bipyridine)ruthenium and bis(2,2'-bipyridine)(5-chloro-1, 10-phenanthroline)ruthenium.

Dyes suitable as a counterion are for example cations of the dye compound of the formula I according to the invention, or cations of triarylmethanes, for example malachite green, indolines, thiazines, for example methylene blue, xanthones, thioxanthones, oxazines, acridines, cyanines, rhodamines, phenazines, for example safranine, preferably cyanines, thioxanthones and safranine. Preferred as a dye counterion is the cation of the dye according to formula I.

X in the formula I preferably is CH, C—CH₃, C—Cl, or C—O—$C_1$–$C_8$alkyl, especially CH.

Ar preferably is a group selected from (A), (C), (D), (E), (F) or (G), in particular (A) and (E).

R in particular is $C_1$–$C_6$alkyl or benzyl, especiylly $C_1$–$C_4$alkyl.

$R_1$ preferably is $C_1$–$C_8$alkoxy, especially $C_1$–$C_4$alkoxy, or $C_1$–$C_8$alkyl.

s preferably is 1.

$R_2$ in particular is hydrogen or $C_1$–$C_4$alkyl, especially hydrogen.

Preferred $R_3$ is hydrogen or $C_1$–$C_4$alkyl.

Y is preferably $C_1$–$C_6$alkoxy, especially $C_1$–$C_4$alkoxy, in particular methoxy.

r in the formula (A) and the groups $$-CH_2-\overset{O}{C}-\phenyl(Y_1)_r \quad \text{and} \quad \phenyl(Y_1)_r$$

is 0 to 5, preferably 2; in the formulae (B), (C), (D),(E), (F), (G), (H), (J) and (K) r is preferably 0, 1 or 2, especially 0.

W preferably is O or S.

Preferred anions L are tosylate, PF₆, or borates, in particular borates of formulae II and X.

Interesting is a photoinitiator system, wherein component a) is a compound of the formula I, wherein X is CH; R is $C_1$–$C_6$alkyl; s is 0; $R_2$ is hydrogen; Ar is a group selected from (A), (B), (D) or (E); Y is $C_1$–$C_6$alkoxy; r is 2; and L is hexafluorophosphate or tosylate;

and component b) is a borate compound of the formula II, wherein $R_4$, $R_5$, $R_6$ and $R_7$ independently of one another are phenyl or naphthyl, which aromatic radicals are unsubstituted or are substituted 1–3 times by unsubstituted or halogen-substituted $C_1$–$C_4$alkyl, or the aromatic radicals are substituted by halogen, or $R_4$, $R_5$, $R_6$ and $R_7$ independently of one another are $C_1$–$C_{12}$alkyl, or are $C_5$–$C_{10}$cycloalkyl; and G is a tetraalkylammonium cation.

Preferred is a photoinitiator system, wherein component a) is a compound of the formula I, wherein X is CH; R is $C_1$–$C_4$alkyl; s is 0; $R_2$ is hydrogen; Ar is a group selected from (A), (B), (D), (E), (G), (H), (J) or (L); Y is $C_1$–$C_6$alkoxy, or two Y are alkoxy and these alkoxy groups form a dioxolane fused to the aryl of the arylstyryl residue; r is 2 or 3; W is O or S; and L is hexafluorophosphate or tosylate; and component b) is a borate compound of the formula II, wherein $R_5$, $R_6$, $R_7$ and $R_8$ independently of one another are phenyl or naphthyl, which aromatic radicals are unsubstituted or are substituted 1–3 times by trifluoromethyl, fluoro or chloro, or $R_4$, $R_5$, $R_6$, $R_7$ and $R_8$ independently of one another are $C_1$–$C_{12}$alkyl, or are $C_5$–$C_{10}$cycloalkyl; and G is a tetraalkylammonium cation or component b) is a borate compound of formula X, wherein $R_{41}$ is cyclopentyl, cyclohexyl, cycloheptyl, cyclooctyl,

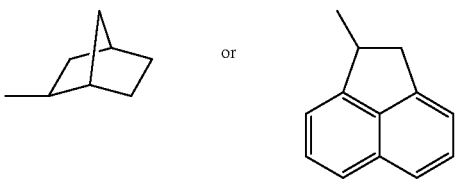

and $R_{40}$ is unsubstituted phenyl or phenyl, which is substituted with fluoro or trifluoromethyl.

This invention provides further a process of producing a polyolefin (as hereinafter defined) by polymerising one or more olefins (as hereinafter defined) under the influence of the free radicals resulting from photolysis of at least one of the photoinitiators or photoinitiator systems according to the present invention. Preferably such polymerisation is effected in conditions such that the cation and anion suffer decomposition to compounds not absorptive of visible light or of light used in the photopolymerisation. Such polymerisation may be applied to such olefins in volume elements of substantial depth, for example involving a light path of up to 50 mm or more.

In accordance with the invention the above described photoinitiator systems, comprising (a) at least one compound of the formula I and optionally (b) an electron donor compound, can be used as photoinitiators for the photopolymerization of ethylenically unsaturated polymerizable compounds and mixtures comprising such compounds. This use can also be implemented in combination with another photoinitiator [C] and/or other additives.

The invention therefore also relates to photopolymerizable compositions comprising

[A] at least one ethylenically unsaturated photopolymerizable compound and

[B] at least one photoinitiator system as described above.

If desired, the composition may contain two or more oxide salts of the formula I with various electron donors or a mixture with one or more other photoinitiator materials.

The composition may comprise additionally to the components [A] and [B] at least one further photoinitiator [C], and/or further coinitiators [D] and/or other additives.

The unsaturated compounds [A] may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes a nd polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and co-polymers thereof, alkyd resins, polybutadiene and butadiene copolymers, polyisoprene and isoprene copolymers, polymers and co polymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)-propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:

trimethylolpropane triacrylate, trimethylolethane triacrylate, trimethylolpropane trimeth-acrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tri-pentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components [A] are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriamine-trismethacrylamide, bis(methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth) acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth) acrylic acid, or may be homo- and copolymers of (meth) acrylates which are esterified with hydroxyalkyl (meth) acrylates. The photopolymerizable compounds can be used alone or in any desired mixtures. It is preferred to use mixtures of polyol (meth)acrylates.

Binders as well can be added to these novel compositions, and this is particularly expedient when the photopolymerizable compounds are liquid or viscous substances. The quantity of binder may, for example, be 5%–95%, preferably 10%–90% and especially 40%–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5000 to 2000000, preferably 10000 to1000000. Examples are: homo- and copolymers of acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly (hexamethylenadipamide), and polyesters such as poly (ethylene glycol terephtalate) and poly(hexamethylene glycol succinate) and polyimides.

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are cross-linked by means of thermal aftertreatment.

It is also possible to add further coinitiators or electron acceptors [D] to the polymerizable composition according to the present invention, for example a neutral, cationic or anionic dye, or an onium salt or a UV absorber.

Component [D] is for example added in an amount from 0.001% to 20%, 0.01% to 10%, especially 0.1% to 5% by weight, based on the composition.

Examples of suitable dyes which can be added as coinitiators [D] are described in U.S. Pat. No. 5,151,520. They are, for example, triarylmethanes, for example malachite green, indolines, thiazines, for example methylene blue, xanthones, thioxanthones, oxazine, acridine or phenazines, for example safranin.

The above-described transition metal complex compounds or onium ion compounds can also be used as coinitiator.

Particularly suitable cationic dyes are malachite green, methylene blue, safranin O, rhodamines of the formula

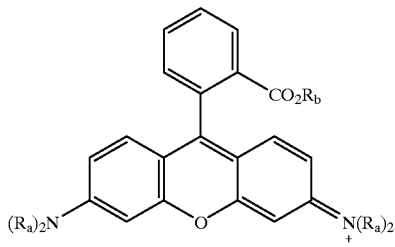

in which $R_a$ and $R_b$ are alkyl radicals or aryl radicals, for example rhodamine B, rhodamine 6G or violamine R, and also sulforhodamine B or sulforhodamine G. Other suitable dyes are fluorones, as described for example by Neckers et al. in J. Polym. Sci., Part A, Poly. Chem, 1995, 33, 1691–1703.

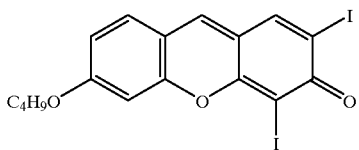

is particularly advantageous. Examples of further suitable dyes are cyanines of the formula

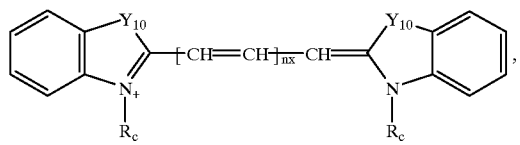

in which $R_c$=alkyl;
nx=0,1,2,3 or 4 and $Y_{10}$=CH=CH, N—$CH_3$, $C(CH_3)_2$, O, S or Se. Preferred cyanines are those in which $Y_{10}$ in the above formula is $C(CH_3)_2$ or S. The following dye compounds are also suitable as coinitiators:

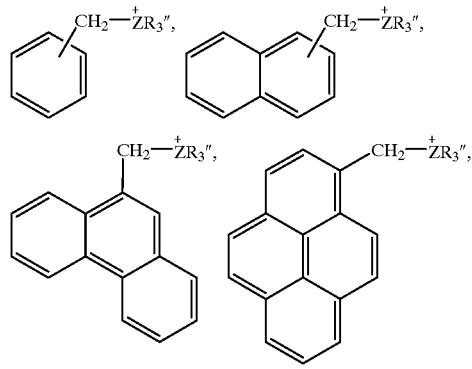

in which Z is P,
N or S and R" is an alkyl or aryl radical. Preferred compounds of the above formulae are those in which $ZR"_3$ is $N(CH_3)_3$, $N(C_2H_5)_3$ or $P(C_6H_5)_3$. Also suitable are compounds such as

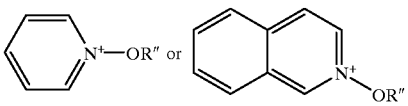

(described by Yagci et al. in J. Polym. Sci. Part A: Polymer Chem. 1992, 30, 1987 and Polymer 1993, 34 (6), 1130) or compounds such as

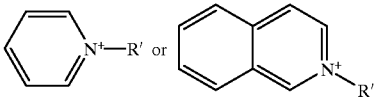

where R'=unsubstituted or substituted benzyl or phenacyl (described in JP-A Hei 7 70221). In these compounds, the aromatic rings in the pyridinium may also be substituted. Other suitable dyes can be found, for example, in U.S. Pat. No. 4,902,604. These are azulene dyes. Of particular advantage as coinitiators are the compounds 1–18 listed in columns 10 and 11 of the above named U.S. patent, in the Table. Examples of further suitable dyes are merocyanine dyes, as described in U.S. Pat. No. 4,950,581 from column 6, line 20 to column 9, line 57. As coinitiators it is also possible to use coumarin or ketocoumarin compounds. Examples of these are given in U.S. Pat. No. 4,950,581 in column 11, line 20 to column 12, line 42 and in JP Hei 06-175557. Further suitable coinitiators are xanthones or thioxanthones as described, for example, in U.S. Pat. No. 4,950,581, column 12, line 44 to column 13, line 15. Further suitable dyes are such bearing more than one positive or negative charge. Examples for dyes bearing more than one positive charge are disclosed in JP Kokai Hei 04-146905.

Anionic dye compounds can also be employed as coinitiators [D]. For instance, Rose Bengal, eosine or fluorescein are also suitable as coinitiators. Other suitable dyes, for example from the triarylmethane class or azo class, are described in U.S. Pat. No. 5,143,818.

Examples of UV absorbers which are suitable as coinitiator [D] are thioxanthone derivatives, coumarins, benzophenone, benzophenone derivatives (e.g. Michler's Ketone, QUANTACURE ABQ, QUANTACURE BPQ and QUANTACURE BTC from International Biosynthetics), or derivatives of hexaarylbisimidazole. Examples of suitable hexaarylbisimidazole derivatives are described, for example, in U.S. Pat. Nos. 3,784,557, 4,252,887, 4,311,783, 4,459,349, 4,410,621 and 4,622,286. Of particular advantage are 2-o-chlorophenyl-substituted derivatives, such as 2,2'-bis(o-chlorophenyl)-4,4',5,5'-tetraphenyl-1,1'-bisimidazole. Other UV absorbers suitable as coinitiators in this context are, for example, polycyclic aromatic hydrocarbons, for example anthracene or pyrene, and the triazines described in EP 137452, in DE 2718254 and in DE 2243621. Further suitable triazines can be found in U.S. Pat. No. 4,950,581, column 14, line 60 to column 18, line 44. Of particular advantage are trihalomethyltriazines, for example 2,4-bis(trichloromethyl)-6—(4-styrylphenyl)-s-triazine (described in JP Hei 01-033548). Other suitable coinitiators are benzoteridinediones (described in JP Hei 02-113002), metal complexes (described in JP Hei 04-261405), porphyrins (described in JP Hei 06-202548 and JP Hei 06-195014), p-aminophenyl compounds (described in EP 475153), xanthenes (described in JP Hei 06-175566) or pyrylium, thiopyrylium and selenopyrylium dyes (described in JP Hei 06-175563). Also suitable as coinitiators are readily reducible compounds. The term readily reducible compound refers in this context also to compounds described in U.S. Pat. No. 4,950,581, including for example iodonium salts, sulfonium salts, or-ganic peroxides, compounds containing carbon halide bonds (trichloromethyltriazines, heterocyclic sulfur compounds and other photoinitiators (a-amino ketones). Examples of other additives are heterocycles as described in the patents and patent applications U.S. Pat. No. 5,168,032, JP Hei 02-244050, JP Hei 02-054268, JP Hei 01-017048 and DE 383308. Examples of further additives are aromatic imines described in U.S. Pat. No. 5,079,126, and aromatic diazo compounds described in U.S. Pat. No. 5,200,292 (e.g. iminoquinone diazides), thiols, described in U.S. Pat. No. 4,937,159 and thiols and N,N-dialkylaniline described in U.S. Pat. No. 4,874,685. Other sensitizers which aresuitable in combination with the photoinitiator system according to the invention are camphor quinone and its derivatives, as well as other diketones. It is also possible to employ two or more of the abovementioned coinitiators and additives in combination.

The invention also provides a composition, wherein the further coinitiator [D] is a dye, which changes or looses colour during or after the irradiation.

In certain cases it may be of advantage to use mixtures of two or more of the novel photoinitiator systems. It is of course also possible to use mixtures with known photoinitiators [C], for example mixtures with benzophenone, acetophenone derivatives, for example α-hydroxycycloalkyl phenyl ketones, dialkoxyacetophenones, α-hydroxy- or α-aminoacetophenones, 4-aroyl-1,3-dioxolanes, benzoin alkyl ethers and benzil ketals, phenylglyoxalic esters, dimeric phenylglyoxalic esters, monoacyl phosphine oxides, bisacylphosphine oxides, trisacylphosphine oxides, titanocenes, ferrocenes, anthraquinone, thioxanthones or xanthones or trichloromethyltriazines.

Examples of particularly suitable photoinitiators [C] are: 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4(2-hydroxyethoxy)-benzoyl]-1-hydroxy-1-methylethane, 1-[4(acryloyloxyethoxy) benzoyl]-1-hydroxy-1-methylethane, diphenyl ketone, phenyl-1-hydroxy-cyclohexyl ketone, (4-morpholinobenzoyl)-1-benzyl-1-dimethylaminopropane, 1-(3,4-di-methoxyphenyl)-2-benzyl-2-dimethylamino-butan-1-one, (4-methylthiobenzoyl)-1-methyl-1-morpholinoethane, benzil dimethyl ketal, phenylglyoxalic acid methylester, bis(cyclopentadienyl)-bis(2,6-difluoro-3-pyrryl-phenyl)titanium, cyclopentadienyl-arene-iron(II) complex salts, for example ($\eta^6$-iso-propylbenzene)($\eta^5$-cyclopentadienyl)iron(II) hexafluorophosphate, (2,4,6-trimethylbenzoyl)diphenylphosphine oxide, bis(2,6-dimethoxy-benzoyl)-(2,4,4-trimethyl-pentyl)phosphine oxide, bis(2,4,6-trimethylbenzoyl)-2,4-dipentoxyphenylphosphine oxide or bis(2,4,6-trimethylbenzoyl)-phenylphosphine oxide and tris(2-methoxybenzoyl)phosphine oxide. Other suitable additional photoinitiators can be found in U.S. Pat. No. 4,950,581 column 20, line 35 to column 21, line 35.

Where the novel photoinitiator systems are employed in hybrid systems, use is made, in addition to the novel free-radical hardener systems, of cationic photoinitiators, e.g. aromatic sulfonium or iodonium salts as described for example in U.S. Pat. No. 4,950,581, column 18, line 60 to column 19, line 10 or cyclopentadienyl-arene-iron(II) complex salts, for example ($\eta^6$-Iso-propylbenzol)($\eta^5$-cyclopentadien-yl)iron(II) hexafluorophosphate. The "onium" salts here serve as electron acceptors:

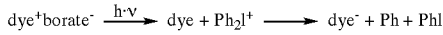

Here an initiating radical (Ph) is obtained from an inactive or terminating radical (dye).

Other additives such as for example

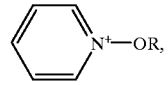

can act in the same way, thereby boosting the photoinitiator activity of the system.

The invention therefore further provides compositions which in addition to the photoinitiator system [B] also comprise at least one further photoinitiator [C] and/or other additives. The photopolymerizable compositions include the photoinitiator system [B] or the mixture of the photoinitiator system [B] and the additional photoinitiator(s) [C] expediently in a quantity of from 0.01% to 15% by weight, for example 0.05% to 15% by weight, preferably from 0.1% to 5% by weight, based on the composition. (The quantity indicated relates to the overall quantity of photoinitiator in the composition.)

Compositions comprising as photoinitiator [C] a titanocene, a ferrocenium salt, a benzophenone, a benzoin alkyl ether, a benzil ketal, a 4-aroyl-1,3-dioxolane, a dialkoxyacetophenone, an α-hydroxy- or α-aminoacetophenone, an α-hydroxycycloalkyl phenyl ketone, a xanthone, a thioxanthone, an anthraquinone, a champhorquinone or a mono- or bisacylphosphine oxide, a trichloromethyltriazine, a phenylglyoxalic ester or a dimeric phenylglyoxalic ester or mixtures thereof, as additional photoinitiator are of particular preference. Especially preferred are combinations with α-aminoacetophenones, for example with (4-morpholinobenzoyl)-1-benzyl-1-dimethylaminopropan or (4-methylthiobenzoyl)-1-methyl-1-morpholinoethan.

Particularly preferred is a composition comprising as photoinitiator [C] an α-amino ketone and an onium compound.

In addition to the photoinitiator the photopolymerizable mixtures may include various additives. Examples of these are thermal inhibitors, which are intended to prevent premature polymerization, examples being hydroquinone, hydroquinine derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS).

Examples of such UV absorbers and light stabilizers are 1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydro-xyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotrizole, 2-(2'-hydroxy-4'-octoxyphenyl)benzotriazole, 2-(3',5'-di-tert-amyl-2'-hydroxyphenyl)benzotriazole, 2-(3',5'-bis-(αmαdimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyl-oxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy- 5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl-phenyl.

2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis-( 1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6, 6-tetramethyl-4-piperidyl)hexa-methylenediamine and 4-tert-octylamino-2,6-dichloro-1,3,5-s-triazine, tris-(2,2,6, 6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro-[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino)-ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2, 5-dione and 3-dodecyl-1-(1,2,2,6,6-penta-methyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyhenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, bis-(2,6-di-tert-butyl-4-methylphenyl) pentaerythrityl diphosphite, bis-isodecyloxy pentaerythrityl diphosphite, bis-(2,4-di-tert-butyl-6-methylphenyl) pentaerythrityl diphosphite, bis-(2,4,6-tri-tert-butylphenyl) pentaerythrityl diphosphite, tristearyl sorbityl triphosphite, tetrakis-(2,4-di-tert-butylphenyl)-4,4'-biphenylene diphosphonite, 6-isooctyloxy-2,4,8,10-tetra-tert-butyl-12H-di-benzo[d,g]-1,3,2-dioxaphosphocine, 6-fluoro-2,4,8,10-tetra-tert-butyl-12-methyl-dibenzo[d,g]-1, 3,2-dioxaphosphocine, bis-(2,4-di-tert-butyl-6-methylphenyl) methyl phosphite and bis(2,4-di-tert-butyl-6-methylphenyl) ethyl phosphite.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309. Photopolymerization can also be accelerated by adding further photosentisizers which shift or broaden the spectral sensitivity. These are, in particular, aromatic carbonyl compounds, for example benzophenone, thioxanthone, anthraquinone and 3-acylcoumarin derivatives, and also 3-(aroylmethylene)thiazolines, but also eosine, rhodamine and erythrosine dyes, as well as all compounds which can be used as coinitiators as described above.

The curing process can be assisted by, in particular, compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

Further customary additives, depending on the intended use, are optical brighteners, fillers, pigments, dyes, wetting agents or levelling assistants.

In order to cure thick and pigmented coatings it is appropriate to add glass microspheres or pulverized glass fibres, as described for example in U.S. Pat. No. 5,013,768.

The choice of additive is made depending on the field of application and on properties required for this field. The additives described above are customary in the art and accordingly are added in amounts which are usual in the respective application.

The invention also provides compositions comprising as component [A] at least one ethylenically unsaturated photopolymerizable compound which is emulsified or dissolved in water. Many variants of such radiation-curable aqueous prepolymer dispersions are commercially available. A prepolymer dispersion is understood as being a dispersion of water and at least one prepolymer dispersed therein. The concentration of water in these systems is, for example, from 5% to 80% by weight, in particular from 30% to 60% by weight. The concentration of the radiation-curable prepolymer or prepolymer mixture is, for example, from 95% to 20% by weight, in particular from 70% to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10 000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one $\alpha,\beta$-ethylenically unsaturated carboxylic acid, of polyurethane (meth)acrylates and of acrylic copolymers which contain $\alpha,\beta$-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2% to 15% and a content of from 0.01 to 0.8 mol of polymerizable C—C double bonds per 100 g of prepolymer. Other suitable aqueous dispersions, based on specific alkyl (meth)acrylate polymers, are described in EP 41125, and suitable water-dispersible, radiation-curable prepolymers of urethane acrylates can be found in DE 2936039.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

The oxide cation salt of the formula I is suitably present in the composition at 0.01% to 5%, preferably from 0.05% to 2% by weight. The electron donor compounds, e.g. the borate may be present at 0.01% to 10%, e.g. 0.01% to 5%, preferably 0.5% to 2% or 0.5% to 1% by weight.

The composition may contain a peroxide such as benzoyl peroxide or a peroxyester such as tert-butyl perbenzoate, at for example 0.01% to 5%, preferably from 0.5% to 1% by weight.

A typical composition contains 0.5% to 12% by weight, especially 1% to 5% by weight of additives, of the polymerizable components as defined above. Important additives include pigments and colouring matters for article identification purposes.

The composition may also comprise additives appropriate for stereolithography.

If any such component absorbs light at a wavelength in part of the range at which photoinitiation takes place, a photoinitiator having absorption outside that part range should preferably be used, so as to permit polymerisation deep into the volume of composition used.

The photopolymerizable compositions can be used for various purposes, for example as printing ink, as a clear finish, as a white finish, for example for wood or metal, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists or permanent resists, for colour filters, and as solder masks for electronic circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and other auxiliaries) and other thick-layered compositions, for coating or sealing electronic components and chips, or as coatings for optical fibres.

The novel photoinitiator systems may additionally be employed as initiators for emulsion polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiator systems and mixtures thereof can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations beng as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics.

In addition to the novel photoinitiator systems, the powder coating formulations may also include UV absorbers. Appropriate examples are listed above in sections 1.–8.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and Gas, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principaly on the type of composition and on the coating technique. The solvent should be inert, i.e. it should not undergo a chemical reaction with the components and should be able to be one, cyclohexanone, N-methylpyrrolidone, dioxane, tetrahydrofuran, 2-methoxyethanol, 2 -ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 μm to more than 100 μm, for example 20 mm or 0.02 to 10 cm, preferably 0.02 to 2 cm.

The novel radiation-sensitive compositions further find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing plates, for use in chemical milling or as a microresist In the production of integrated circuits. The novel composition may further be employed as photoimageable dielectrics, encapsulation materials for chips and isolating layers. The possible layer supports, and the processing conditions of the coating substrates, are just as varied.

The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits a re silicon wafers. The layer thicknesses for photographic materials and offset printing formes is generally from about 0.5 μm to 10 μm, while for printed circuits it is from 1.0 μm to about 1 00 μm.

Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computercontrolled electron beams. It is also possible to use masks made of liquid crystals that can be adressed pixel by pixel to generate digital images, as is, for example, described by A. Bertsch, J. Y. Jezequel, J. C. Andre in Journal of Photochemistry and Photobiology A: Chemistry 1997, 107, p. 275–281 and by K. -P. Nicolay in Offset Printing 1997, 6, p. 34–37.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqeos solutions.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K. -P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The novel compounds and photoinitiator systems can also be used as a toner in a formulation as described e.g. in JP Hei 7-140718.

Further, the compounds and photoinitiator systems according to the present invention can be used to decolorize colored materials, as described for example in JP Hei 6-299106 or in photodecolorizing recording material as described for example in JP Hei 5-61247 or JP Hei 2-190383.

The new compounds can also be used in recording materials as described for example in the U.S. Pat. No. 4,842,980, 4,865,942 or 4,532,200. They may further be used in microcapsule systems together with latent dyes, as described for example in JP Hei 4-255848 or JP Hei 5-318909, or in multicolor systems as described in JP Hei 2-190386, JP Hei 2-190385, JP Hei 2-44 or JP Hei 2-223446.

The curing by means of the compounds and photoinitiator systems according to the present invention is in general initiated by electromagnetic radiation.

The photosensitivity of the novel compositions can, depending upon the added components, extend in general from about 200 nm through the UV region into the infrared region and therefore spans a very broad range. The quinolinium dyes of formula I according to the present invention have wavelenghts absorptions not greater than 600 nm. Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays, produced by means of synchrotrons or laser plasma. The distance between the lamp and the substrate to be exposed in accordance with the invention may vary depending on the intended application and the type and output of lamp, and may be, for example, from 2 cm to 150 cm. Laser light sources, for example excimer lasers, such as krypton F lasers for exposure at 248 nm are also suitable. Lasers in the visible region and in the IR region can also be employed. By this method it is possible to produce printed circuits in the electronics industry, lithographic offset printing plates or relief printing plates, and also photographic image recording materials. Preferably lasers emitting between 400 and 900 nm (e.g. argon ion laser, frequency doubled Nd/YAG) are employed as light sources.

The invention therefore also provides a process for the photopolymerization of monomeric, oligomeric or polymeric compounds containing at least one ethylenically unsaturated double bond, which comprises adding to the abovementioned compounds at least one photoinitiator system as described above and irradiating the resulting composition with electromagnetic radiation.

The invention additionally provides compositions for producing pigmented and nonpigmented paints and varnishes, powder coatings, printing inks, printing plates, adhesives, dental compositions, waveguides, optical switches, colour proofing systems, colour filters, glass fibre cable coatings, screen printing stencils, resist materials, composite compositions, decolorizing materials, decolorizing materials for image recording materials, for image recording materials using microcapsules, for photographic reproductions, for encapsulating electrical and electronic components, for producing magnetic recording materials, for producing three-dimensional objects by means of stereolithography, and as image recording material, especially for holographic recordings.

The invention further provides a coated substrate which is coated on at least one surface with a composition as described above, and describes a process for the photographic production of relief images, in which a coated substrate is subjected to imagewise exposure and then the unexposed portions are removed with a solvent. Of particular advantage in this context is the laser beam exposure already mentioned above.

The invention provides particularly a procedure of forming a polymer coating on a continuous strand or web of material by passing the strand or web through: at least one application zone in which the composition according to the invention is applied to it; and at least one irradiation zone in which the applied composition is caused to polymerise.

As a result of the rapid action of the photoinitiator, the residence time in each zone can be short enough to permit continuous operation at high line speeds. As a result of the deep polymerisation made possible by the non-absorbing decomposition of the photoinitiator, a single or multiple application can be followed by a single irradiation to produce coatings of thickness in the range 0.02 to 2 cm, even the achievement of higher thicknesses is possible with the novel photoinitiator systems and compositions comprising the same.

A particular product of the procedure is an optical fibre comprising a glass-fibre and a coating of titania-pigmented acrylic polymer.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

A) Preparation of dye salts (Examples 1–12)

EXAMPLE 1

Preparation of

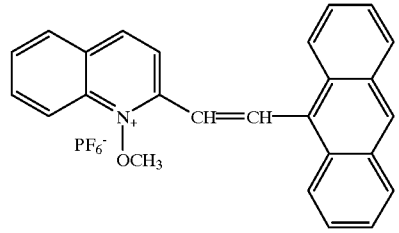

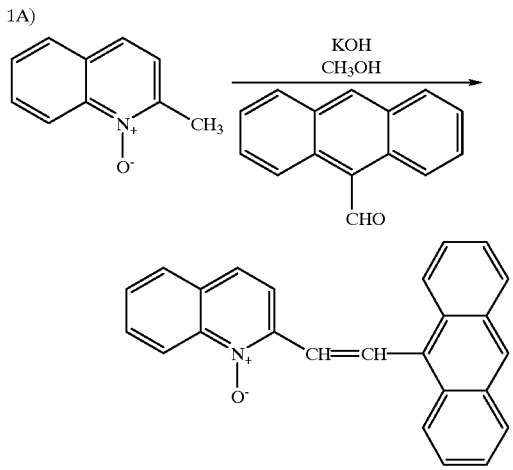

A mixture of 3.18 g (0.02 mol) of quinaldine N-oxide, 4.54 g (0.022 mol) of 9-anthracenecarbo aldehyde and 0.56 g KOH in methanol (30 ml) is heated at reflux for 3 h. The reaction mixture is allowed to cool, then poured into 50 ml of water and the resulting suspension is filtered. The solid is washed with 50 ml of methanol/water (1:1) and dried. Chromatography on silica gel (3:1 Hexane:ethyl acetate) gives 0.85 g of the desired anthracene derivative with a melting point of 220–223° C.

1B)

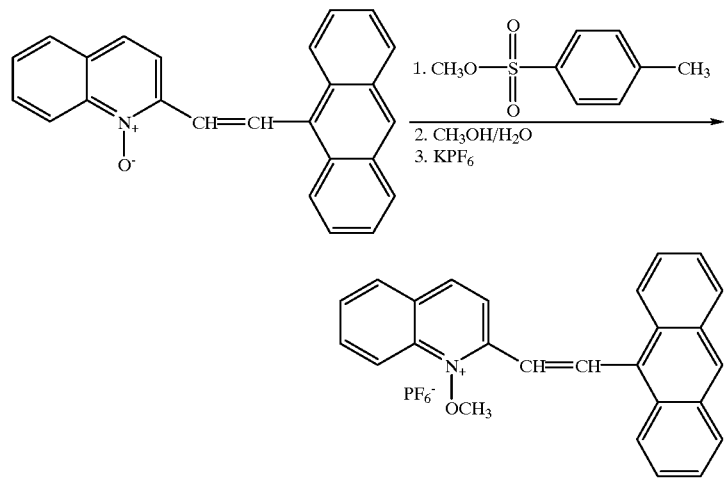

A mixture of 0.84 g (0.0024 mol) of the compound as prepared by method 1A and 4.47 g (0.24 mol) of methyl tosylate is heated for 0.5 h at 100° C. After cooling, the solid mass is treated with 50 ml of methanol/water (1:1) and the resulting suspension is filtered. Treatment of the filtrate with an excess of $KPF_6$ leads to the precipitation of a deep violet solid. The solid is filtered off, washed with 20 ml of methanol/water (1:1) and 50 ml of ether. The residue is then dried overnight under vacuum to give 1.0 g (82%) of the desired compound with a melting point of 184–186° C.

EXAMPLES 2–5

The compounds of the examples 2–5 are prepared according to the method described in example 1, using the appropriate starting materials. The strucutres and $\lambda_{max}$ data are listed in the following table 1.

TABLE 1

| example | Ar | L | melting point [° C.] | $\lambda_{max}$ [nm] |
|---|---|---|---|---|
| 1 | 9-anthryl | $PF_6$ | 184–186 | 480 |
| 2 | 1-naphthyl (methyl-substituted) | $PF_6$ | 187–189 | 399 |
| 3 | pyridyl-phenyl | —O—$SO_2$—C$_6$H$_4$—CH$_3$ | 198–199 | 400 |
| 4 | dimethoxy-methylphenyl | —O—$SO_2$—C$_6$H$_4$—CH$_3$ | * | 449 |

TABLE 1-continued

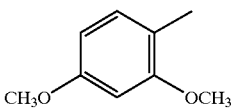

| example | Ar | L | melting point [° C.] | $\lambda_{max}$ [nm] |
|---------|----|----|---------------------|---------------------|
| 5 | (2,4-dimethoxyphenyl with CH₃) | PF₆ | 194–198 | 437 |

* not determined

EXAMPLE 6

Preparation of

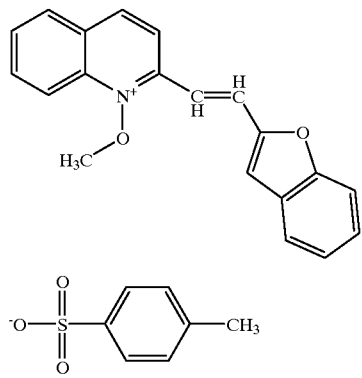

A solution of 8.0 g (0.05 mol) of quinaldine N-oxide, 5.9 g (0.04 mol) 2-formyl-benzofuran and 1.4 g (0.025 mol) of KOH in methanol (60 ml) is heated under reflux for 4.5 h. The reaction mixture is allowed to cool to ambient temperature (RT) and then poured into water (200 ml). The yellow solid which precipitates is filtered, washed with water then dried under vacuum to give 10.0 g (0.035 mol, 87%) of the desired condensation product: mp 175–176° C.; shift δ [ppm] in $^1$H-NMR (CDCl$_3$): 8.71 (d, 1, J=8.7 Hz), 8.00–7.42 (m, 9), 7.26 (t, 1, J=8.0 Hz), 7.15 (t, 1, J=7.4 Hz) and 6.82 (s, 1).

The condensation product and 20.0 g (0.105 mol) of methyl p-toluenesulfonate are heated at 100–110° C. for 0.5 h. The viscous red resin is treated with 1:1 methanol:water (100 ml) and the precipitated orange solid is collected by filtration. The solid is washed with 1:1 methanol/water and dried under vacuum to give 11.7 g (0.25 mol, 71%) of the N-methoxyquinolium dye: mp 185–189° C.; shift δ [ppm] in $^1$H NMR (DMSO-d$_6$): 8.56 (d, 1, J=8.6 Hz), 8.17–7.63 (m, 9), 7.50 (d, 2, J=8.1 Hz), 7.39 (t, 1, J=7.3 Hz), 7.28 (t, 1, J=7.5 Hz), 7.24 (s, 1), 7.12 (d, 2, J=8.1 Hz), 5.11 (s, 3) and 2.28 (s, 3). $\lambda_{max}$ 381 nm.

Preparation of the hexafluorophosphate salts

The crude tosylate salt is dissolved in 1:1 methanol:water and two equivalents of KPF$_6$ are added with stirring. The resulting precipitate is collected by filtration, washed with 1:1 methanol:water and dried under vacuum to afford the desired N-methoxyquinolinium hexafluorophosphate.

EXAMPLES 7–12

The compounds of examples 7–12 are prepared according to the method provided in example 6, employing the corresponding educts. The compounds and their physical data are collected in table 2 below.

TABLE 2

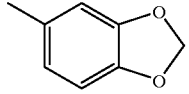

| example | Ar | melting point [° C.] | $\lambda_{max}$ [nm] |
|---------|----|---------------------|---------------------|
| 7 | 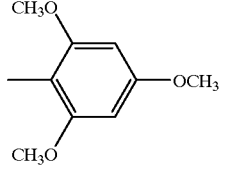 | >200 | 436 |
| 8 | 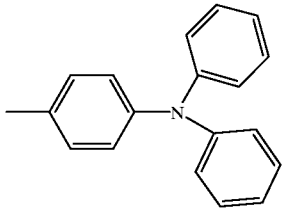 | >200 | 460 |
| 9 | 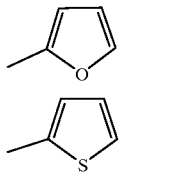 | >200 | 524 |
| 10 | (furyl methyl) | * | 421 |
| 11 | 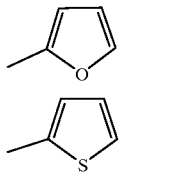 | 186–193 | 419 |

TABLE 2-continued

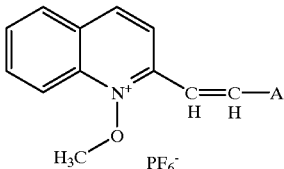

| example | Ar | melting point [° C.] | $\lambda_{max}$ [nm] |
|---|---|---|---|
| 12 | 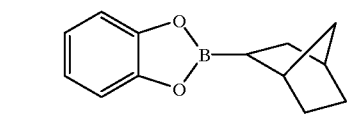 | * | 422 |

* not determined

B) Preparation of borates (Examples B1–B8 and Examples 13–29)
Preparation of the Starting Materials (Examples B1–B8)

EXAMPLE B1
Dimethyl cyclohexylboronate

To a suspension of 10.2 g (0.27 mol) of $NaBH_4$ in 101.4 ml (82.15 g, 1.0 mol) of cyclohexen and 330 ml of absoluted tetrahydrofurane (THF) 45.3 ml (51.1 g, 0.36 mol) of $BF_3$-diethyletherate are added dropwise during 45 min. The reaction temperature is held below 30° C. by an external water bath. After the addition the reaction mixture is first stirred at ambient temperature for 1.5 h and is then heated for 3 h to about 50° C. The resulting suspension is filtered under argon-flow and concentrated under vacuum. 86 g of a white solid are obtained. The solid is heated to 130° C. (temperature of the bath 140° C.) and 74 ml (67.5 g, 0.65 mol) of trimethylborate are added during 5.5 h. During the addition the internal temperature decreases from 130° C. to 108° C. Then the reaction mixture is heated for 12 h at reflux, and the internal temperature raises to 120° C. The reaction mixture is allowed to cool down to ambient temperature and treated with 5 ml of methanol. Distillation at 4 mbar affords 92.7 g (0.61 mol, 61%) of a colourless liquid: Kp 37° C. (Lit.: Douglass et al *J. Amer. Chem. Soc.* 1964, 86, 5431).

EXAMPLE B2
Dimethyl cyclopentylboronate

The title compound is prepared according to the method described in example B1.
Yield: 39%; Kp 31° C. (4 mbar); $^1H$ NMR ($CDCl_3$) d 3.48 (s, 6) and 1.72–1.08 (m, 9) ppm.

EXAMPLE B3
Dimethyl cycloheptylboronate

The title compound is prepared according to the method described in example B1.
Yield: 64%; Kp 56–57° C. (4 mbar); $^1H$ NMR ($CDCl_3$) d 3.47 (s, 6) and 1.71–1.02 (m, 13) ppm.

EXAMPLE B4
Dimethyl Cyclooctylboronat

The title compound is prepared according to the method described in example B1.

Yield: 52%; Kp 68–72° C. (5 mbar); $^1H$ NMR ($CDCl_3$) d 3.48 (s, 6) and 1.72–1.10 (m, 15) ppm.

EXAMPLE B5
Dimethyl endo and exo 2-bicyclo[2.2.1]heptylboronate

The title compound is prepared according to the method described in example B1.
Yield: 64%; Kp 49–50° C. (4 mbar).
(Lit.: Brown et al *Organometallics* 1983, 2, 1311)

EXAMPLE B6
1,2-Phenylen endo and exo 2-bicyclo[2.2.1]heptylboronate

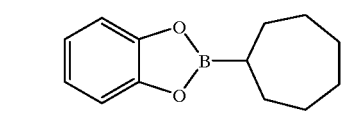

A mixture of 9.66 g (0.103 mol) bicyclo[2.2.1]heptene and 13.5 g (0.113 mol) of 1,3,2-benzodioxaborole (cathecholborane) are heated for 4 h to about 100° C. Destillation of the residue results in obtaining 10.5 g (48%) of a colourless liquid; Kp: 104–110° C. (0.5 mbar); $^{11}B$-NMR ($CDCl_3$) 40.5 ppm.
(Lit.: Brown et al *J. Amer. Chem. Soc.* 1975, 97, 5249.)

EXAMPLE B7
1,2-Phenylen cycloheptylboronate

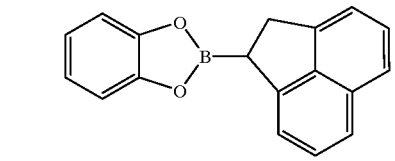

The title compound is prepared according to the method described in example B6.
Yield: 36%; Kp: 110–114° C. (0.1 mbar); $^{11}B$ NMR ($CDCl_3$) 36.0 ppm.

EXAMPLE B8
1,2-Phenylen 1-acenaphthenylboronate

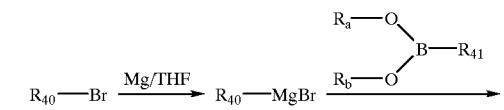

The title compound is prepared according to the method described in example B6.
Yield: 30%; Kp: 180–185° C. (0.4 mbar); $^{11}B$ NMR ($CDCl_3$) 28.9 ppm.

EXAMPLE 13
General procedure for preparing the trisaryl-cycloalkyl borates according to the invention from the corresponding boronates:

$$R_{40}-Br \xrightarrow{Mg/THF} R_{40}-MgBr \quad \begin{matrix} R_a-O \\ R_b-O \end{matrix}B-R_{41} \longrightarrow$$

-continued

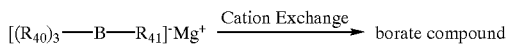

Preparation of tetramethylammonium tris(3-fluorophenyl)-cyclopentyl borate

A small part of 7.0 g (0.04 mol) of 1-bromo-3-fluorobenzene is added to a suspension of 0.97 g (0.04 mol) of magnesium turnings in 20 ml of tetrahydrofuran (THF). The reaction mixture is heated until the Grignard reaction sets in. When reaction begins, heating is discontinued and the remainder of the 1-bromo-3-fluorobenzene is added dropwise over 20 minutes in such a way that gentle reflux is maintained. Following this addition, heating is continued until the rest of the magnesium has been consumed. After the Grignard solution has been cooled to room temperature, 0.006 mol of the compound of example B2 are added stepwise. After the end of this addition, the reaction mixture is heated at reflux for 2 hours. Subsequently, the mixture is concentrated in vacuo and the residue is treated with 40 ml of saturated sodium chloride salt solution. The resulting emulsion is extracted with ethyl acetate, and the organic phases are dried over magnesium sulfate, filtered and concentrated. The resulting residue is dissolved in 80 ml of a 1:1 mixture of methanol and water. Following filtration and treatment of the filtrate with 1.4 g (0.013 mol) of tetramethylammonium chloride a solid is precipitated. This solid is filtered off, treated with boiling methanol and dried in vacuo, giving the borate of the invention in ayield of 80% with a melting point 168–176° C. The shift value δ in the $^{11}$B-NMR spectrum in $CD_3COCD_3$ is −3.41 ppm.

EXAMPLES 14–29

The compounds of examples 14–29 are prepared according to the method described above in example 13. Exchanging the 1-brom-3-fluorophenyl with the corresponding arylbromide ($R_{40}$—Br) and employing the corresponding boronate. The compounds, the corresponding starting materials (boronates) and the physical data are collected in table 3.

TABLE 3

$$R_{40}-\underset{\underset{R_{40}}{|}}{\overset{\overset{R_{40}}{|}}{B^-}}-R_{41}\ G^+$$

| Example | $R_{40}$ | $R_{41}$ | $G^+$ | boronate | mp *1 $^{11}$B-NMR *2 yield |
|---|---|---|---|---|---|
| 14 | 3-(trifluoro-methyl)-phenyl | cyclopentyl | $N(CH_3)_4$ | B2 | <20 −3.29 80% |
| 15 | 3-fluorophenyl | ![acenaphthyl] | $N(CH_3)_4$ | B8 | >220 −1.45 35% |
| 16 | 3-fluorophenyl | cyclohexyl | $N(CH_3)_4$ | B1 | >230 -3.06 79% |
| 17 | 3-(trifluoro-methyl)-phenyl | cyclohexyl | $N(CH_3)_4$ | B1 | 90–92 −2.97 34% |
| 18 | 2-methyl-phenyl | cyclohexyl | $N(CH_3)_4$ | B1 | >200 −3.12 10% |
| 19 | phenyl | ![norbornyl] | $N(CH_3)_4$ | B5 | >230 −3.10, −4.29 71% |
| 20 | 3-fluorophenyl | ![norbornyl] | $N(CH_3)_4$ | B5 | 188–189 — 74% |
| 21 | 3-fluorophenyl | ![norbornyl] | $N(C_4H_9)_4$ | B6 | 127–129 −3.12, −4.30 59% |

TABLE 3-continued $$R_{40}-\overset{R_{40}}{\underset{R_{40}}{B^{-}}}-R_{41} \ G^{+}$$

| Example | $R_{40}$ | $R_{41}$ | $G^+$ | boronate | mp *1 11B-NMR *2 yield |
|---|---|---|---|---|---|
| 22 | 3-(trifluoro-methyl)-phenyl | | $N(CH_3)_4$ | B5 | 70–72 −3.02, −4.18 72% |
| 23 | phenyl | cycloheptyl | $N(CH_3)_4$ | B3 | >230 −2.29 74% |
| 24 | 3-fluorophenyl | cycloheptyl | $N(CH_3)_4$ | B3 | 229–231 * 79% |
| 25 | 3-fluorophenyl | cycloheptyl | $N(C_4H_9)_4$ | B7 | 155–156 −2.29 30% |
| 26 | 3-(trifluoro-methyl)-phenyl | cycloheptyl | $N(CH_3)_4$ | B3 | 77–80 −2.24 47% |
| 27 | phenyl | cyclooctyl | $N(CH_3)_4$ | B4 | >230 −1.78 63% |
| 28 | 3-fluorophenyl | cyclooctyl | $N(CH_3)_4$ | B4 | 229–231 −1.77 60% |
| 29 | 3-(trifluoro-methyl)-phenyl | cyclooctyl | $N(CH_3)_4$ | B4 | 77–80 −1.72 27% |

\* not determined
\*1 melting point in ° C.
\*2 shift δ in 11B-NMR spectrum in ppm, measured in acetone-$d_6$ C) Application Examples (30–41)

In application examples 30–33 the following borate compounds are used as sensitizers:

a

[structure: tris(3-fluorophenyl)(hexyl)borate tetramethylammonium]

b

[structure: tris(2,4,6-trimethylphenyl)(1-naphthyl)borate N(CH$_3$)$_2$(C$_{10}$H$_{21}$)$_2$]

c

[structure: triphenyl(hexyl)borate tetramethylammonium]

d

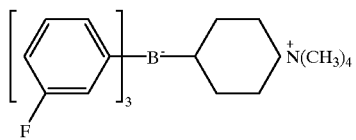

compound of example 16 e

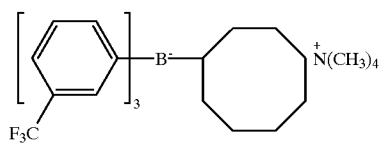

compound of example 29 g

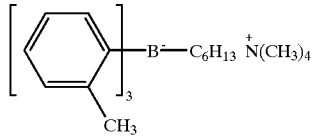

h

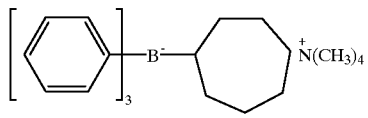

compound of example 23

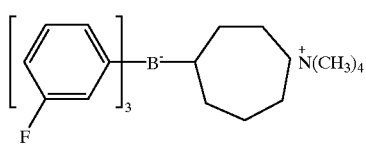

compound of example 24

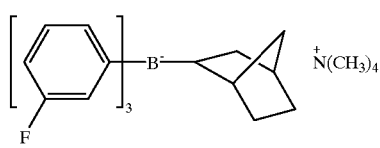

compound of example 20

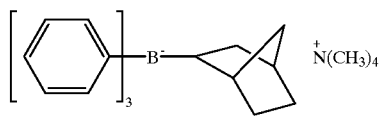

compound of example 19

EXAMPLE 30

A photocurable formulation is prepared by mixing the following components:

| | |
|---|---|
| 10.0 g | of dipentaerythritol monohydroxypentaacrylate, ® SR 399, Sartomer Co., Berkshire, GB |
| 15.0 g | of tripropylene glycol diacrylate, Sartomer Co., Berkshire, GB |
| 15.0 g | of N-vinylpyrrolidone, Fluka |
| 10.0 g | of trimethylolpropane triacrylate, Degussa |
| 50.0 g | of urethane acrylate ® Actylan AJ20, Société Nationale des Poudres et Explosifs |
| 0.3 g | of levelling assistant ® Byk 300, Byk-Mallinckrodt |

Portions of this composition are mixed with the novel photoinitiator system, comprising 0.3% of a compound of the formula I and 0.4% of a borate compound as electron donor compound. All operations are carried out under red light. The samples are applied to a 300 μm aluminum foil. To this film there is applied a 76 μm thick polyester film, over which a standardized test negative having 21 steps of different optical density (Stouffer wedge) is placed. The sample is covered with a second UV-transparent film and compressed on a metal plate by means of vacuum. Exposure is carried out for 20 seconds, using a 4 kW xenon lamp at a distance of 30 cm. Following exposure, the cover films and the mask are removed and the exposed film is developed in ethanol for 10 seconds at 23° C. in an ultrasound bath. Drying is carried out at 40° C. in a convection oven for 5 minutes. The sensitivity of the initiator system used is characterized by indicating the last wedge step which is reproduced (i.e. polymerized) without tack. The higher the number of steps, the more sensitive is the system tested. The results are summarized in Table 4.

TABLE 4

| Dye compound of Example | Borate Compound | Number of steps reproduced |
|---|---|---|
| 4 | a | 14 |
| 2 | a | 14 |
| 4 | b | 16 |
| 3 | b | 16 |
| 5 | b | 16 |
| 4 | h | 15 |
| 3 | l | 16 |
| 3 | k | 15 |

EXAMPLE 31

A photocurable composition is prepared from

| | |
|---|---|
| 45.1 g | of ® Scripset 540 (styrene-maleic anhydride copolymer, Monsanto) |
| 48.3 g | of trimethylolpropane triacrylate |
| 6.6 g | of polyethylene glycol diacrylate |
| 150.0 g | of acetone |

Portions of this composition are mixed with the photoinitiator system to be tested, comprising 0.3% of a compound of the formula I and 0.4% of a borate compound as electron donor compound.

The mixture is stirred at room temperature for 1–2 hours in order to dissolve the photoinitiator system. All operations are carried out under red light. The samples to which initiator has been added are applied to 300 μm aluminium foil (10×15 cm). The solvent is removed by drying at room temperature for 5 minutes and then heating at 60° C. in a convection oven for 15 minutes. Over the liquid film there is placed a 76 μm thick polyester film, on which is laid a standardized test negative with 21 steps of different optical density (Stouffer wedge). A second polyester film is applied over this assembly, and the resulting laminate is fixed on a metal plate. The sample is then exposed for 40 seconds using a 4 kW xenon lamp at a distance of 30 cm. Following exposure the cover films and the mask are removed, and the exposed film is developed with 0.85% strength aqueous sodium carbonate solution in an ultra-sound bath and then dried at 40° C. in a convection oven for 5 minutes. The sensitivity of the initiator system used is characterized by indicating the last wedge step reproduced without tack. The higher the number of steps, the more sensitive the system. The results are reproduced in Table 5.

TABLE 5

| Dye compound of Example | Borate Compound | Number of steps reproduced |
|---|---|---|
| 3 | a | 17 |
| 4 | a | 16 |
| 5 | a | 16 |
| 3 | k | 19 |
| 3 | d | 18 |
| 3 | e | 16 |

EXAMPLE 32

A photocurable composition is prepared by mixing the following components:

| | |
|---|---|
| 37.64 g | of ® Sartomer SR 444, pentaerythritol triacrylate, (Sartomer Company, Westchester) |
| 10.76 g | of ® Cymel 301, hexamethoxymethylmelamine (American Cyanamid, USA) |
| 47.30 g | of ® Carboset 525, thermoplastic polyacrylate containing carboxyl groups (B. F. Goodrich) |
| 4.30 g | of polyvinylpyrrolidone PVP (GAF, USA) |
| 100.00 g | of this composition are mixed with |
| 319.00 g | of methylene chloride and |
| 30.00 g | of methanol. |

Samples of this composition are mixed with the photoinitiator system comprising 0.3% of a compound of the formula I and 0.4% of a borate compound as electron donor (based on the solids content), by stirring at room temperature for one hour. All operations are carried out under red light. The samples to which the initiator system has been added are applied to a 300 μm aluminium foil (10×15 cm). The solvent is removed by first drying at room temperature for 5 minutes and then heating at 60° C. for 15 minutes in a convection oven, to give a dry film thickness of 35 μm. A 76 μm thick polyester film is placed on the liquid film, and a standardized test negative with 21 steps of different optical density (Stouffer wedge) is placed over this. The sample is covered with a second UV-transparent film and is fixed on a metal plate by means of vacuum. The sample is then exposed for 40 seconds using a 4 kW xenon lamp at a distance of 30 cm. After exposure, the cover films and the mask are removed and the exposed film is developed for 240 seconds with 1% strength aqueous sodium carbonate solution in an ultrasound bath and then dried at 60° C. in a convection oven for 15 minutes. The sensitivity of the initiator system used is characterized by indicating the last wedge step reproduced without tack. The higher the number of steps, the more sensitive the system. The results are given in Table 6.

TABLE 6

| Dye compound of Example | Borate Compound | Number of steps reproduced |
|---|---|---|
| 4 | a | 15 |
| 3 | a | 15 |
| 2 | a | 14 |
| 5 | a | 14 |
| 5 | b | 17 |
| 4 | b | 16 |
| 3 | b | 15 |
| 3 | g | 19 |
| 3 | c | 17 |
| 3 | i | 16 |
| 3 | l | 16 |

EXAMPLE 33

The following experiments are performed with a formulation containing

| | |
|---|---|
| 85.00 parts | of acetone, |
| 2.55 parts | of Scripset 540 (styrene-maleic anhydride copolymer, Monsanto), |
| 1.50 parts | of polyethylene glycol diacrylate, |
| 10.95 parts | of trimethylolpropane triacrylate, and as photoinitiator |
| 0.40 parts | of a borate salt and |
| 0.30 parts | of a compound of the formula I. |

After addition of the initiators to be tested the solution is spincoated onto anodized aluminum foils at a speed of 5000 rpm. After drying at room temperature for 1 minute a solution consisting of 15 parts of polyvinylalcohol (Mw=15.000) in 10.62 parts of isopropanol and 74.38 parts of distilled water is coated on top of the film at a speed of 5000 rpm. This sample is then irradiated with a 532 nm laser beam of 58 mW power at different writing speeds. Development is performend in a 1% Na$_2$CO$_3$ solution in water using a spray developer for 1 minute. The sensitivity of the system is evaluated by determination of the highest writing speed that could be employed to form lines that withstood the developing. The results are reported in table 7.

TABLE 7

| Dye compound of Example | Borate Compound | Speed [cm/s] |
|---|---|---|
| 1 | n | 624 |
| 1 | h | 624 |
| 1 | g | 624 |
| 5 | c | 432 |

In application examples 34–37 the following borate compounds are used

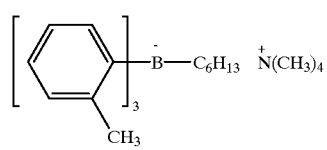

m

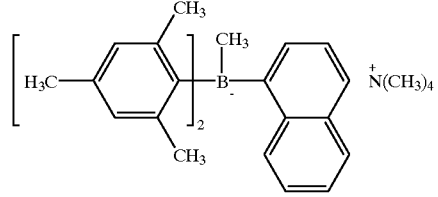

n

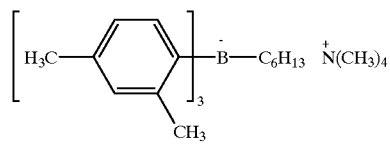

o

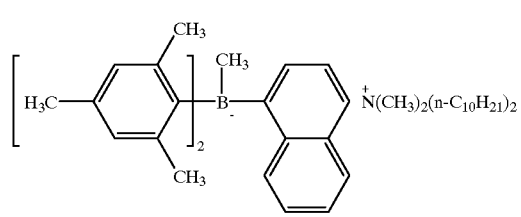

p

-continued

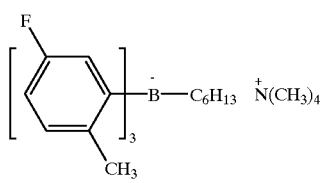

r

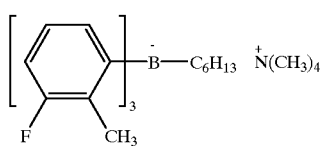

s

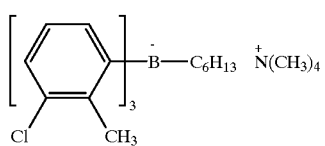

t

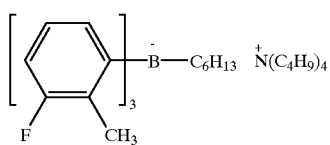

u

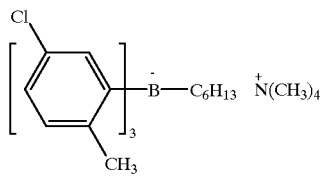

v

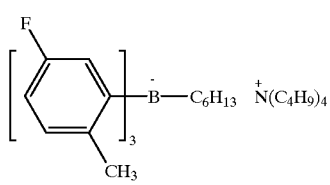

w

EXAMPLE 34

A photocurable formulation is prepared by mixing the following components:

---

10.0 g of dipentaerythritol monohydroxypentaacrylate, ® SR 399, Sartomer Co., Berkshire, GB
15.0 g of tripropylene glycol diacrylate, Sartomer Co., Berkshire, GB
15.0 g of N-vinylpyrrolidone, Fluka
10.0 g of trimethylolpropane triacrylate, Degussa
50.0 g of urethane acrylate ® Actylan AJ20, Société Nationale des Poudres et Explosifs
0.3 g of levelling assistant ® Byk 300, Byk-Mallinckrodt

---

Portions of this composition are mixed with 0.4%, based on the total quantity of the formulation, of the respective borate compound and 0.3% of the respective coinitiator. All operations are carried out under red light. The formulations are applied to a 300 μm aluminium foil. The thickness of the dry film is 60 μm. Over the film there is placed a 76 pm thick polyester film, on which is laid a standardized test negative with 21 steps of different optical density (Stouffer wedge). A second polyester film is applied over this assembly, and the resulting laminate is fixed on a metal plate. The sample is then exposed for 20 seconds using a 4 kW xenon lamp at a distance of 30 cm. Following exposure, the cover films and the mask are removed and the exposed film is developed in ethanol in an ultrasound bath at 23° C. for 10 seconds. Drying is carried out at 40° C. in a convection oven for 5 minutes. The sensitivity of the initiator system used is characterized by indicating the last wedge step reproduced without tack. The higher the number of steps, the more sensitive the system. The results are produced in Table 8.

TABLE 8

| Dye Compound of Example | Borate Compound | Number of Steps reproduced |
| --- | --- | --- |
| 7 | n | 18 |
| 7 | m | 18 |
| 8 | n | 19 |
| 8 | o | 18 |
| 8 | m | 19 |
| 8 | p | 19 |
| 9 | n | 21 |
| 9 | o | 18 |
| 9 | m | 18 |
| 9 | p | 19 |
| 12 | n | 18 |

EXAMPLE 35

Photocuring of an acrylate mixture

A photocurable composition is prepared from

---

45.1 g of ® Scripset 540 (styrene-maleic anhydride copolymer, Monsanto)
48.3 g of trimethylolpropane triacrylate
6.6 g of polyethylene glycol diacrylate
150.0 g of acetone

--- and in each case 0.4% of the respective borate compound and 0.3% of the respective dye are added. The mixture is stirred at room temperature for 1–2 hours in order to dissolve the photoinitiator. All operations are carried out under red light. The samples to which initiator has been added are applied to 300 μm aluminium foil (10×15 cm). The solvent is removed by drying at room temperature for 5 minutes and then heating at 60° C. in a convection oven for 15 minutes. Over the liquid film there is placed a 76 μm thick polyester film, on which is laid a standardized test negative with 21 steps of different optical density (Stouffer wedge). A second polyester film is applied over this assembly, and the resulting laminate is fixed on a metal plate. The sample is then exposed for 40 seconds using a 4 kW xenon lamp at a distance of 30 cm. Following exposure the cover films and the mask are removed, and the exposed film is developed with 0.85% aqueous sodium carbonate solution in an ultrasound bath and then dried at 40° C. in a convection oven for 5 minutes. The sensitivity of the initiator system used is characterized by indicating the last wedge step reproduced without tack. The higher the number of steps, the more sensitive the system. The results are collected in Table 9.

TABLE 9

| Dye Compound of Example | Borate Compound | Number of Steps reproduced |
| --- | --- | --- |
| 8 | r | 21 |
| 8 | s | 21 |
| 8 | t | 20 |

TABLE 9-continued

| Dye Compound of Example | Borate Compound | Number of Steps reproduced |
|---|---|---|
| 8 | u | 20 |
| 8 | v | 19 |
| 9 | r | 21 |
| 9 | s | 21 |
| 9 | t | 20 |
| 9 | u | 20 |
| 9 | v | 20 |
| 9 | w | 19 |

EXAMPLE 36

Reactivity test in a solder resist

A photocurable composition is prepared by mixing the following components:

| | |
|---|---|
| 37.64 g | of trimethylolpropane trisacrylate |
| 10.76 g | of ® Cymel 301, hexamethoxymethylmelamine (American Cyanamid, USA) |
| 47.30 g | of ® Carboset 525, thermoplastic polyacrylate containing carboxyl groups (B. F. Goodrich) |
| 4.30 g | of polyvinylpyrrolidone PVP (GAF, USA) |
| 319.00 g | of methylene chloride and |
| 30.00 g | of methanol. |

Portions of this composition are mixed with in each case 0.4% of the borate compound and 0.3% of the respective coinitiator, based on the solids content. All operations are carried out under red light. The samples to which initiator has been added are applied in a dry-film thickness of 35 μm aluminium foil (10×15 cm). The solvent is removed by heating at 60° C. in a convection oven for 15 minutes. Onto the liquid film there is placed a 76 μm thick polyester film, over which a standardized test negative with 21 steps of different optical density (Stouffer wedge) is applied. The sample is covered with a second UV-transparent film and is pressed on a metal plate by means of vacuum. The sample is then exposed for 40 seconds using a MO61/5 kW lamp at a distance of 30 cm. Following exposure, the cover films and the mask are removed and the exposed film is developed with 0.85% aqueous sodium carbonate solution in an ultrasound bath for 240 seconds and is then dried at 60° C. in a convection oven for 15 minutes. The sensitivity of the initiator system used is characterized by indicating the last wedge step reproduced without tack. The higher the number of steps, the more sensitive the system. The results are collected in Table 10.

TABLE 10

| Dye compound of Example | Borate Compound | Number of Steps reproduced |
|---|---|---|
| 7 | n | 21 |
| 7 | o | 20 |
| 8 | n | 20 |
| 8 | o | 20 |
| 8 | m | 20 |
| 9 | n | 21 |
| 9 | o | 21 |
| 9 | m | 20 |
| 9 | p | 21 |
| 12 | n | 21 |

TABLE 10-continued

| Dye compound of Example | Borate Compound | Number of Steps reproduced |
|---|---|---|
| 12 | o | 20 |
| 12 | m | 19 |

EXAMPLE 37

Laser Direct Imaging experiments

The laser experiments were performed in a formulation containing

| | |
|---|---|
| 75.0 parts | of acetone, |
| 2.5 parts | of ® Scripset 540 (styrene-maleic anhydride copolymer, Monsanto) |
| 10.0 parts | of ® Actilane 200 (aliphatic urethane acrylate, Akros) |
| 1.5 parts | of pentaethylene-glycol diacrylate and |
| 11.0 parts | of trimethylolpropane trisacrylate. |

After addition of the initiators (0.4% of the respective borate compound, 0.3% of the respective coinitiator compound at concentrations based on the solids content) the solution is spincoated onto anodized aluminum foils at a speed of 5000 rpm. After drying at room temperature for 1 minute a solution consisting of 15 parts of polyvinylalcohol (Mw=15.000) in 10.62 parts of isopropanol and 74.38 parts of distilled water is coated on top of the film at a speed of 5000 rpm. The sample is then irradiated with a 532 nm laser beam of a power of 16 mW and at different writing speeds. After development for 1 minute in a 1% $Na_2CO_3$ solution in water using a spray developer, the highest writing speed at which a line is formed is recorded. The higher the writing speed, the higher is the reactivity of the initiator. The results are collected in Table 11.

TABLE 11

| Dye Compound of Example | Borate Compound | Speed [cm/s] |
|---|---|---|
| 9 | n | 480 |
| 9 | o | 432 |
| 9 | m | 480 |

In application examples 38–41 the following coinitiator/sensitizer compounds are used:

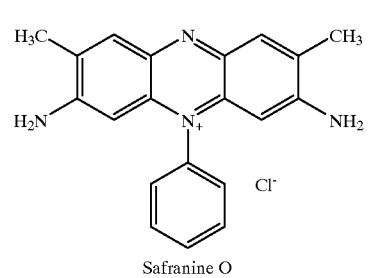

Safranine O

-continued

B compound of example 4

C compound of example 3

D compound of example 9

F

Methylene Blue

-continued

H compound of example 8

EXAMPLE 38

A photocurable formulation is prepared by mixing the following components:

- 10.0 g of dipentaerythritol monohydroxypenta acrylate, ®SR 399, Sartomer Co., Berkshire, GB
- 15.0 g of tripropylene glycol diacrylate, Sartomer Co., Berkshire, GB
- 15.0 g of N-vinylpyrrolidone, Fluka
- 10.0 g of trimethylolpropane triacrylate, Degussa
- 50.0 g of urethane acrylate ®Actylan AJ20, Société Nationale des Poudres et Explosifs
- 0.3 g of levelling assistant ®Byk 300, Byk-Mallinckrodt Portions of this composition are mixed with 0.4%, based on the total quantity of the formulation, of the respective borate compound and 0.3% of the respective coinitiator. All operations are carried out under red light. The formulations are applied to a 300 μm aluminium foil. The thickness of the dry film is 60 μm. Over the film there is placed a 76 μm thick polyester film, on which is laid a standardized test negative with 21 steps of different optical density (Stouffer wedge). A second polyester film is applied over this assembly, and the resulting laminate is fixed on a metal plate. The sample is then exposed for 20 seconds using a 4 kW xenon lamp at a distance of 30 cm. Following exposure, the cover films and the mask are removed and the exposed film is developed in ethanol in an ultrasound bath at 23° C. for 10 seconds. Drying is carried out at 40° C. in a convection oven for 5 minutes. The sensitivity of the initiator system used is characterized by indicating the last wedge step reproduced without tack. The higher the number of steps, the more sensitive the system. The results are collected in Table 12.

TABLE 12

| Borate of example | Dye | number of steps |
| --- | --- | --- |
| 23 | A | 14 |
| 27 | A | 14 |
| 23 | B | 15 |
| 16 | B | 13 |
| 24 | B | 13 |
| 26 | B | 13 |
| 23 | C | 15 |
| 27 | C | 16 |
| 19 | C | 16 |
| 24 | C | 15 |
| 20 | C | 15 |
| 19 | D | 16 |
| 20 | D | 15 |
| 20 | E | 17 |
| 24 | E | 17 |
| 20 | G | 16 |
| 24 | G | 15 |
| 18 | H | 19 |
| 18 | K | 20 |

EXAMPLE 39
Photocuring of an acrylate mixture

A photocurable composition is prepared from

> 45.1 g of ®Scripset 540 (styrene-maleic anhydride copolymer, Monsanto)
> 48.3 g of trimethylolpropane triacrylate
> 6.6 g of polyethylene glycol diacrylate
> 150.0 g of acetone and in each case 0.4% of the respective borate photoinitiator compound (0.7% of the borate in combination with coinitiator F) and 0.3% of the respective coinitiator are added. The mixture is stirred at room temperature for 1–2 hours in order to dissolve the photoinitiator. All operations are carried out under red light. The samples to which initiator has been added are applied to 300 μm aluminum foil (10×15 cm). The solvent is removed by drying at room temperature for 5 minutes and then heating at 60° C. in a convection oven for 15 minutes. Over the liquid film there is placed a 76 μm thick polyester film, on which is laid a standaridized test negative with 21 steps of different optical density (Stouffer wedge). A second polyester film is applied over this assembly, and the resulting laminate is fixed on a metal plate. The sample is then exposed for 40 seconds using a 4 kW xenon lamp at a distance of 30 cm. Following exposure the cover films and the mask are removed, and the exposed film is developed with 0.85% aqueous sodium carbonate solution in an ultrasound bath and then dried at 40° C. in a convection oven for 5 minutes. The sensitivity of the initiator system used is characterized by indicating the last wedge step reproduced without tack. The higher the number of steps, the more sensitive the system. The results are reproduced in Table 13.

TABLE 13

| Borate of example | Dye | number of steps |
|---|---|---|
| 20 | A | 19 |
| 26 | A | 16 |
| 29 | A | 16 |
| 22 | A | 16 |
| 13 | H | 21 |
| 25 | H | 20 |
| 21 | H | 19 |
| 13 | F | 21 |
| 25 | F | 21 |
| 21 | F | 21 |

EXAMPLE 40
Reactivity test in a solder resist

A photocurable composition is prepared by mixing the following components:

> 37.64 g of trimethylolpropane trisacrylate
> 10.76 g of ®Cymel 301, hexamethoxymethylmelamine (American Cyanamid, USA)
> 47.30 g of ®Carboset 525, thermoplastic polyacrylate containing carboxyl groups (B. F. Goodrich)
> 4.30 g of polyvinylpyrrolidone PVP (GAF, USA)
> 319.00 g of methylene chloride and
> 30.00 g of methanol.

Portions of this composition are mixed with in each case 0.4% of the respective borate compound and 0.3% of the respective coinitiator, based on the solids content. All operations are carried out under red light. The samples to which initiator has been added are applied in a dry-film thickness of 35 μm aluminium foil (10×15 cm). The solvent is removed by heating at 60° C. in a convection oven for 15 minutes. Onto the liquid film there is placed a 76 μm thick polyester film, over which a standardized test negative with 21 steps of different optical density (Stouffer wedge) is applied. The sample is covered with a second UV-transparent film and is pressed on a metal plate by means of vacuum. The sample is then exposed for 40 seconds using a MO61/5 kW lamp at a distance of 30 cm. Following exposure, the cover films and the mask are removed and the exposed film is developed with 0.85% aqueous sodium carbonate solution in an ultrasound bath for 240 seconds and is then dried at 60° C. in a convection oven for 15 minutes. The sensitivity of the initiator system used is characterized by indicating the last wedge step reproduced without tack. The higher the number of steps, the more sensitive the system. The results are collected in Table 14.

TABLE 14

| Borate of example | Dye | number of steps |
|---|---|---|
| 23 | A | 19 |
| 27 | A | 18 |
| 19 | A | 19 |
| 28 | A | 17 |
| 19 | D | 16 |
| 16 | D | 15 |
| 24 | D | 16 |

EXAMPLE 41
Laser Direct Imaging experiments

The laser experiments were performed in a formulation containing

> 75.0 parts of acetone,
> 2.5 parts of ®Scripset 540 (styrene-maleic anhydride copolymer, Monsanto)
> 10.0 parts of ®Actilane 200 (aliphatic urethane acrylate, Akros)
> 1.5 parts of pentaethylene-glycol diacrylate and
> 11.0 parts of trimethylolpropane trisacrylate.

After addition of the initiators (0.4% of the respective borate compound, 0.3% of the respective coinitiator compound at concentrations based on the solids content) the solution is spin-coated onto anodized aluminum foils at a speed of 5000 rpm. After drying at room temperature for 1 minute a solution consisting of 15 parts of polyvinylalcohol (Mw=15.000) in 10.62 parts of isopropanol and 74.38 parts of distilled water is coated on top of the film at a speed of 5000 rpm. The sample is then irradiated with a 532 nm laser beam of a power of 16 mW and at different writing speeds. After development for 1 minute in a 1% $Na_2CO_3$ solution in water using a spray developer, the highest writing speed at which a line is formed is recorded. The higher the writing speed, the higher is the reactivity of the initiator. The results are collected in Table 15.

TABLE 15

| Borate of example | Dye | writing speed [cm/s] |
|---|---|---|
| 15 | H | 28.8 |
| 27 | H | 28.8 |
| 18 | H | 48.0 |

What is claimed is:

1. A photoinitiator system comprising (a) at least one compound of the formula I

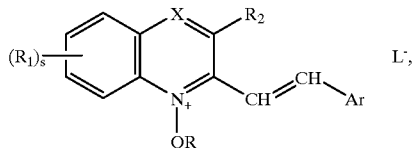
(I)

wherein

X is CH, C—CH$_3$, C—Cl, C—O—C$_1$–C$_8$alkyl or $^+$NOR L$^-$;

R is C$_1$–C$_6$alkyl, benzyl, CH$_2$COOR$_3$ or a group

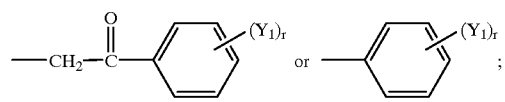

R$_1$ is C$_1$–C$_8$alkoxy, C$_1$–C$_{12}$alkyl, halogen, NO$_2$, benzyloxy or phenyloxy, wherein the phenylring in the benzyloxy or phenyloxy group is unsubstituted or substituted by C$_1$–C$_{12}$alkyl, C$_1$–C$_6$alkoxy, halogen or CF$_3$;

s is 0 to 4;

R$_2$ is hydrogen, C$_1$–C$_8$alkoxy, C$_1$–C$_{12}$alkyl, benzyloxy or phenyloxy, wherein the phenylring in the benzyloxy or phenyloxy group is unsubstituted or substituted by C$_1$–C$_{12}$alkyl, C$_1$–C$_6$alkoxy, halogen or CF$_3$;

R$_3$ is hydrogen, C$_1$–C$_{12}$alkyl or benzyl;

Ar is a group selected from (A), (B), (C), (D), (E), (F), (G), (H), (J), (K) or (L)

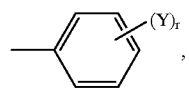
(A)

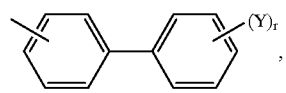
(B)

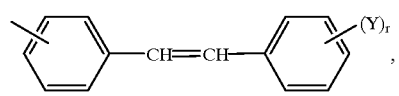
(C)

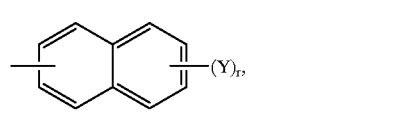
(D)

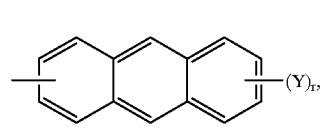
(E)

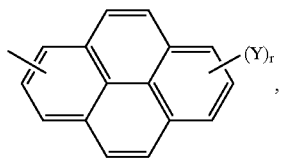
(F)

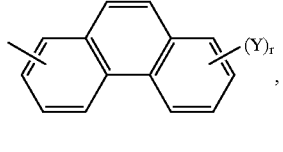
(G)

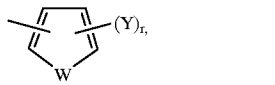
(H)

(J)

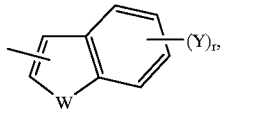
(K)

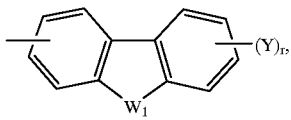
(L)

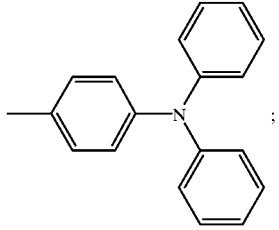

Y is unsubstituted or C$_1$–C$_6$alkoxy-substituted C$_1$–C$_6$alkyl, or Y is C$_1$–C$_6$alkoxy, halogen, CF$_3$, NO$_2$, CF$_3$O, benzyloxy or phenyloxy, wherein the phenylring in the benzyloxy or phenyloxy group is unsubstituted or substituted by C$_1$–C$_{12}$alkyl, C$_1$–C$_6$alkoxy, halogen or CF$_3$ or, if r is two or more and two Y are alkoxy these alkoxy groups may form a dioxolane or dioxane fused to the aryl of the arylstyryl residue;

Y$_1$ is unsubstituted or C$_1$–C$_6$alkoxy-substituted C$_1$–C$_6$alkyl, or Y$_1$ is C$_1$–C$_6$alkoxy, halogen, CF$_3$, NO$_2$, CF$_3$O, benzyloxy or phenyloxy, wherein the phenylring in the benzyloxy or phenyloxy group is unsubstituted or substituted by C$_1$–C$_{12}$alkyl, C$_1$–C$_6$alkoxy, halogen or CF$_3$;

W is O, S or CH$_2$;

W$_1$ is O, S, C(R$_4$)$_2$ or CO;

R$_4$ is hydrogen, C$_1$–C$_8$alkoxy, C$_1$–C$_{12}$alkyl, benzyloxy or phenyloxy, wherein the phenylring in the benzyloxy or phenyloxy group is unsubstituted or substituted by C$_1$–C$_{12}$alkyl or C$_1$–C$_6$alkoxy;

r in the formula (A) and the groups

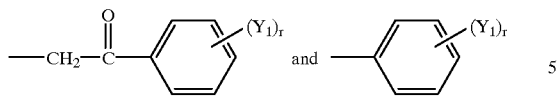

is 0 to 5, in the formulae (B), (C), (E), (F) and (G) is 0 to 9, in the formula (D) is 0 to 7, in the formula (H) is 0 to 3, in the formula (J) is 0 to 5 and in the formula (K) is 0 to 7; with the proviso, that, if Ar is a group (A), R is $C_1$–$C_6$alkyl, benzyl, $CH_2COOR_3$ or a group

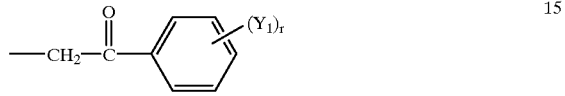

and X is not $^+$NOR L$^-$, r is 2 to 5; and

L is an anion; and optionally (b) at least one electron donor compound.

2. A photoinitiator system according to claim 1, wherein the electron donor compound (b) is a borate, thiol, amine, organotin compound, phosphine, arsine, sulfinate, carboxylate or aluminate.

3. A photoinitiator system according to claim 2, wherein the borate is a compound of the formula II or IIa

wherein $R_5$, $R_6$, $R_7$ and $R_8$ independently of one another are phenyl or another aromatic hydrocarbon, with or without any heteroatoms, which aromatic radicals are unsubstituted or are substituted 1–5 times by unsubstituted or halogen-, $OR_{10}$— or $R_{11}R_{12}$N-substituted $C_1$–$C_{20}$alkyl, $C_2$–$C_{20}$alkyl which is interrupted by one or more radicals O, S(O)$_p$ or $NR_{13}$, or the aromatic radicals are substituted by $OR_{10}$, $R_{10}S(O)_p$, $R_{10}S(O)_2$O, $R_{11}R_{12}$N, $R_{10}OC(O)$, $R_{11}R_{12}NC(O)$, $R_{14}C(O)$, $R_{14}R_{15}R_{16}$Si, $R_{14}R_{15}R_{16}$Sn, halogen, CN, $R_{14}R_{15}P(O)_q$, CN and/or

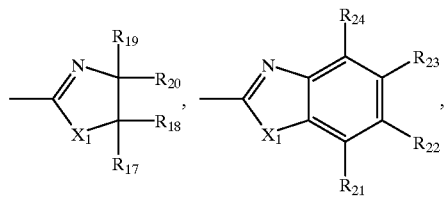

-continued

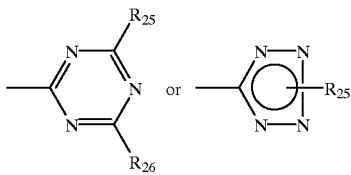

or the radicals $R_5$ and $R_6$ form bridges to produce structures of the formula IV, IVa or IVb

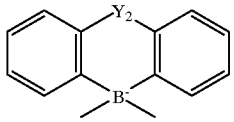

(IV)

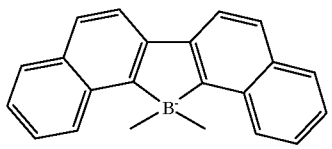

(IVa)

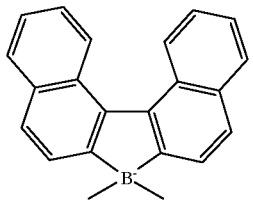

(IVb)

whose aromatic rings are unsubstituted or are substituted by $C_1$–$C_{20}$alkyl, by $C_2$–$C_{20}$alkyl which is interrupted by one or more radicals O, S(O)$_p$ or $NR_{13}$, or the aromatic rings are substituted by $OR_{10}$, $R_{10}S(O)_p$, $R_{10}S(O)_2$O, $R_{11}R_{12}$N, $R_{10}OC(O)$, $R_{11}R_{12}NC(O)$, $R_{14}C(O)$, $R_{14}R_5R_{16}$Si, halogen, CN, $R_{14}R_{15}P(O)_q$ and/or $R_{14}R_{15}R_{16}$Sn, or $R_5$, $R_6$, $R_7$ and $R_8$ independently of one another are $R_{14}R_{15}R_{16}$Si, or $R_5$, $R_6$, $R_7$ and $R_8$ independently of one another are $C_1$–$C_{20}$alkyl, $C_2$–$C_{20}$alkyl which is interrupted by one or more radicals O, S(O)$_p$ or $NR_{13}$, or is $C_3$–$C_{12}$cycloalkyl, $C_2$–$C_8$alkenyl, $R_5$, $R_6$, $R_7$ and $R_8$ independently of one another are $C_1$–$C_{20}$alkyl, $C_2$–$C_{20}$alkyl which is interrupted by one or more radicals O, S(O)$_p$ or $NR_{13}$, or is $C_3$–$C_{12}$cycloalkyl, $C_2$–$C_8$alkenyl, phenyl-$C_1$–$C_6$alkyl or naphthyl-$C_1$–$C_3$alkyl, where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or are substituted by $OR_{10}$, $R_{10}S(O)_p$, $R_{10}S(O)_2$O, $R_{11}R_{12}$N, $R_{10}C(O)$, $R_{11}R_{12}NC(O)$, $R_{14}C(O)$, $R_{14}R_{15}R_{16}$Si, $R_{14}R_{15}R_{16}$Sn, halogen, $R_{14}R_{15}P(O)_q$, and/or CN;

$R_9$ is a divalent aromatic hydrocarbon radical which is unsubstituted or is substituted by $C_1$–$C_6$alkyl, $OR_{10}$, $R_{10}S(O)_p$, $R_{10}S(O)_2$O, $R_{11}R_{12}$N, $R_{10}OC(O)$, $R_{11}R_{12}NC(O)$, $R_{14}C(O)$, $R_{14}R_{15}R_{16}$Si, CN or halogen, or Rg is phenyl-$C_1$–$C_6$alkylene;

E is $R_{27}R_{28}R_{29}$P, $R_{10}R_{11}R_{12}$N or $R_{10}R_{30}$S;

$R_{27}$, $R_{28}$ and $R_{29}$ independently of one another are $C_1$–$C_{12}$alkyl, $C_2$–$C_{12}$alkenyl or $C_3$–$C_{12}$cycloalkyl, where the radicals $C_1$–$C_{12}$alkyl, $C_2$–$C_{12}$alkenyl and $C_3$–$C_{12}$cycloalkyl are unsubstituted or are substituted by $R_{10}OCO$ or CN, or $R_{27}$, $R_{28}$ and $R_{29}$ are unsubstituted or mono- to penta-$C_1$–$C_6$alkyl-, —$C_1$–$C_{12}$alkoxy- or -halogen-substituted phenyl-$C_1$–$C_6$alkyl or are unsubstituted or mono- to penta-$C_1$–$C_6$alkyl-, —$C_1$–$C_{12}$alkoxy- or -halogen-substituted phenyl;

$Y_2$ is $(CH_2)_x$, CH=CH, C(O), $NR_{13}$, O, $S(O)_p$ —$CR_{31}R_{32}$—;

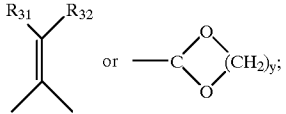

x is 0, 1, 2 or 3;
y is 2 or 3;
p is 0, 1 or 2;
q is 0 or 1;
$R_{10}$ and $R_{30}$ independently of one another are unsubstituted or halogen-substituted $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;
$R_{11}$, and $R_{12}$ independently of one another are hydrogen, unsubstituted or $C_1$–$C_{12}$alkoxy-, halogen-, OH—, $COOR_{10}$— or CN-substituted $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen, or $R_{11}$ and $R_{12}$, together with the N atom to which they are attached, form a 5- or 6-membered ring which may additionally contain O or S atoms;
$R_{13}$ is hydrogen, $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;
$R_{14}$, $R_{15}$ and $R_{16}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;
$R_{17}$, $R_{18}$, $R_{19}$ and $R_{20}$ independently of one another are hydrogen, unsubstituted or $C_1$–$C_{12}$alkoxy-substituted $C_1$–$C_{12}$alkyl, unsubstituted or mono- to penta-$C_1$–$C_6$alkyl-, -$C_1$–$C_{12}$alkoxy- or -halogen-substituted phenyl-$C_1$–$C_6$alkyl or are unsubstituted or mono- to penta-$C_1$–$C_6$alkyl-, —$C_1$–$C_{12}$alkoxy- or -halogen-substituted phenyl, or any two of the radicals $R_{17}$, $R_{18}$, $R_{19}$ and $R_{20}$ together form an aromatic ring to which further aromatic rings may be fused;
$R_{21}$, $R_{22}$, $R_{23}$, $R_{24}$, $R_{25}$ and $R_{26}$ independently of one another are hydrogen, unsubstituted or $C_1$–$C_{12}$alkoxy-, OH— or halogen-substituted $C_1$–$C_{12}$alkyl or are unsubstituted or $C_1$–$C_{12}$alkyl-, $C_1$–$C_{12}$alkoxy-, OH— or halogen-substituted phenyl;

$R_{31}$, and $R_{32}$ are $C_1$–$C_6$alkyl or phenyl, or $R_{31}$, and $R_{32}$, together with the C atom to which they are attached, form a 5- or 6-membered ring;

$X_1$ is N, S or O; and

G is a radical which is able for form positive ions.

4. Photoinitiator system according to claim 3, wherein component a) is a compound of the formula I, wherein X is CH; R is $C_1$–$C_4$alkyl; s is 0; $R_2$ is hydrogen; Ar is a group selected from (A), (B), (D), (E), (G), (H), (J) or (L); Y is $C_1$–$C_6$alkoxy, or two Y are alkoxy and these alkoxy groups form a dioxolane fused to the aryl of the arylstyryl residue; r is 2 or 3; W is O or S; and L is hexafluorophosphate or tosylate; and component b) is a borate compound of the formula II, wherein $R_5$, $R_6$, $R_7$ and $R_8$ independently of one another are phenyl or naphthyl, which aromatic radicals are unsubstituted or are substituted 1–3 times by trifluoromethyl, fluoro or chloro, or $R_4$, $R_5$, $R_6$, $R_7$ and $R_8$ independently of one another are $C_1$–$C_{12}$alkyl, or are $C_5$–$C_{10}$cycloalkyl; and G is a tetraalkylammonium radical.

5. A photoinitiator system according to claim 2, wherein the borate is a compound of the formula III

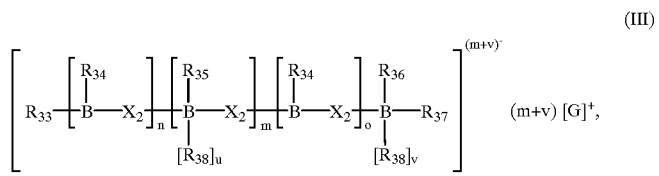

wherein n, m and o are each a number from 0 to 50, but are not simultaneously 0;

u and v are 0 or 1, and at least one of the indices u and v is 1;

$R_{33}$, $R_{34}$, $R_{35}$, $R_{36}$ and $R_{37}$ independently of one another are phenyl or another aromatic hydrocarbon, which radicals are unsubstituted or are substituted by unsubstituted or halo-, $OR_{10}$— and /or $NR_{11}R_{12}$-substituted $C_1$–$C_6$alkyl, or are substituted by $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, $P(O)_qR_{14}R_{15}$, CN or halogen;

p is 0, 1 or 2;

q is 0 or 1;

$R_{38}$ is $C_1$–$C_{12}$alkyl, $C_3$–$C_{12}$cycloalkyl, $C_2$–$C_8$alkenyl, phenyl-$C_1$–$C_6$alkyl or naphthyl-$C_1$–$C_3$alkyl, the radicals $C_1$–$C_{12}$alkyl, $C_3$–$C_{12}$cycloalkyl, $C_2$–$C_8$alkenyl, phenyl-$C_1$–$C_6$alkyl or naphthyl being unsubstituted or substituted by $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$,

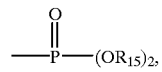

$SiR_{14}R_{15}R_{16}$, $BR_{39}R_{40}$, CN or halogen, or $R_{38}$ is phenyl or another aromatic hydrocarbon radical, which radicals are unsubstituted or substituted by $C_1$–$C_6$alkyl, $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, CN or halogen, at least one of the radicals $R_{33}$, $R_{34}$, $R_{35}$, $R_{36}$ and $R_{37}$ being a phenyl radical which is substituted ortho to the bond to the boron atom, or being another aromatic hydrocarbon radical which is sterically hindered ortho to the boron atom;

$R_{10}$, $R_{11}$, $R_{12}$, $R_{13}$, $R_{14}$, $R_{15}$, $R_{16}$ are as defined above for the formula 11;

$R_{39}$ and $R_{40}$ independently of one another are as defined for $R_{10}$ or are $C_3$–$C_{12}$cycloalkyl, or together with the B atom to which they are attached, form a 5- or 6-membered ring;

$X_2$ is $C_1$–$C_{20}$alkylene which is unsubstituted or substituted by $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, CN, halogen or $P(O)_qR_{14}R_{15}$, or $X_2$ is $C_3$–$C_{12}$cycloalkylene or $C_2$–$C_8$alkenylene, each of which is unsubstituted or substituted by $OR_{10}$, $S(O)_p R_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, CN or halogen, or where these radicals are interrupted by one or more groups —O—, —S(O)$_p$— or —NR$_{13}$—, or $X_2$ is a divalent aromatic hydrocarbon radical which is unsubstituted or substituted by $C_1$–$C_6$alkyl, $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, CN, halogen, or $X_2$ is $C_1$–$C_{20}$alkylene which is interrupted by one or more groups —O—, —S(O)$_p$— or —NR$_{13}$—, or $X_2$ is a radical of the formula V or VI (V)

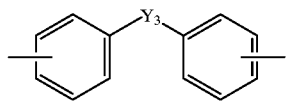

(VI)

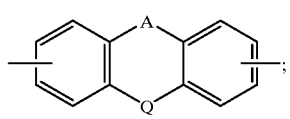

$Y_3$ is —(CH$_2$)$_x$—, —C(O)—, —NR$_{13}$—, —O—, —S(O)$_p$—, —CR$_{31}$R$_{32}$—, —CH=CH—,

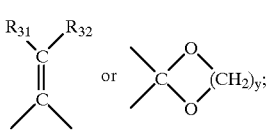

x is 0, 1, 2 or 3;
y is 2 or 3;

$R_{31}$ and $R_{32}$ are $C_1$–$C_6$alkyl or phenyl, or $R_{31}$ and $R_{32}$, together with the C atom to which they are attached, form a 5- or 6-membered ring;

A and Q independently of one another are a direct bond, —(CH$_2$)$_x$—, —CH=CH—, —C(O)—, —NR$_{13}$—, —S(O)$_p$—, —CR$_{31}$R$_{32}$—,

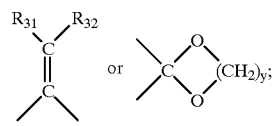

or the radicals $R_{33}$, $R_{34}$, $R_{35}$, $R_{36}$ and $X_2$ form bridges to produce radicals of the formula (VII) or (VIII)

(VII)

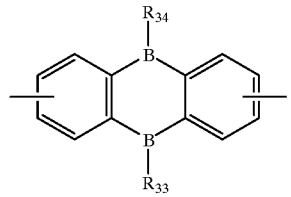

(VIII)

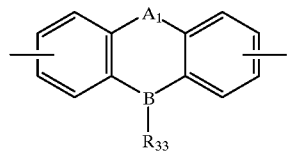

$A_1$ is —(CH$_2$)$_t$—, —CH=CH—, —C(O)—, —NR$_{13}$—, —O—, —S(O)$_p$—, —CR$_{31}$R$_{32}$—,

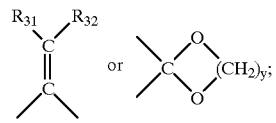

t is 0, 1 or 2;

the radicals of the formulae (V), (VI), (VII) and (VIII) being unsubstituted or being substituted on the aromatic rings by $OR_{10}$, $S(O)_pR_{10}$, $OS(O)_2R_{10}$, $NR_{11}R_{12}$, $C(O)OR_{10}$, $C(O)NR_{11}R_{12}$, $C(O)R_{14}$, $SiR_{14}R_{15}R_{16}$, $BR_{39}R_{40}$, CN or halogen and where additional phenyl rings may be fused to the phenyl rings of the formulae (V), (VI), (VII) and (VIII);

G is a radical which is able to form positive ions.

6. Photoinitiator system according to claim 2, wherein the borate is a compound of formula X (X)

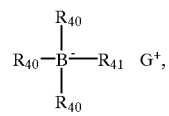

wherein $R_{40}$ is phenyl which is unsubstituted or substituted 1–5 times by halogen, $C_1$–$C_4$alkoxy, $C_1$–$C_{20}$alkyl or $C_1$–$C_{20}$haloalkyl;

$R_{41}$ is $C_3$–$C_{12}$cycloalkyl, which may be condensed with one or more aromatic rings; and G is a radical which is able to form positive ions.

7. Photoinitiator system according to claim 6, wherein component a) is a compound of the formula I, wherein X is CH; R is $C_1$–$C_4$alkyl; s is 0; $R_2$ is hydrogen; Ar is a group selected from (A), (B), (D), (E), (G), (H), (J) or (L); Y is $C_1$–$C_6$alkoxy, or two Y are alkoxy and these alkoxy groups form a dioxolane fused to the aryl of the arylstyryl residue; r is 2 or 3; W is O or S; and L is hexafluorophosphate or tosylate; and component b) is a borate compound of formula X, wherein $R_{41}$ is cyclopentyl, cyclohexyl, cycloheptyl, cyclooctyl,

 or 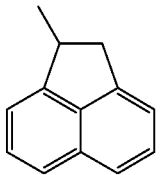

and $R_{41}$ is unsubstituted phenyl or phenyl, which is substituted with fluoro or trifluoromethyl.

8. A composition comprising
[A] at least one ethylenically unsaturated polymerizable compound and
[B] at least one photoinitiator system according to claim 1.

9. A composition according to claim 8, comprising additionally to components [A] and [B] at least one further photoinitiator [C], and/or further coinitiators [D] and/or other additives.

10. A composition according to claim 9, comprising a titanocene, a ferrocenium salt, a benzophenone, a benzoin alkyl ether, a benzyl ketal, a 4-aroyl-1,3-dioxolane, a dialkoxyacetophenone, an α-hydroxy- or α-aminoacetophenone, an α-hydroxycycloalkyl phenyl ketone, a phenylglyoxalic ester, a xanthone, a thioxanthone, an anthraquinone, a champhorquinone or a mono-, bis- or trisacylphosphine oxide, or mixtures thereof, as additional photoinitiator [C].

11. A composition according to claim 9, wherein the further coinitiator [D] is a a neutral, cationic or anionic dye or an onium salt.

12. A composition according to claim 11, wherein the further coinitiator [D] is a dye, which changes or looses colour during or after the irradiation.

13. A composition according to claim 9, comprising as photoinitiator [C] an α-amino ketone and as coinitiator [D] an onium compound.

14. A composition according to claim 8, comprising from 0.01 to 15% by weight of component [B], based on the composition.

15. A process for the photopolymerization of monomeric, oligomeric or polymeric compounds containing at least one ethylenically unsaturated double bond, which comprises adding at least one photoinitiator system according to claim 1 to said compounds and irradiating the resulting composition with electromagnetic radiation.

16. A process for the photopolymerization of monomeric, oligomeric or polymeric compounds containing at least one ethylenically unsaturated double bond, for producing pigmented and nonpigmented paints and varnishes, powder coatings, printing inks, printing plates, adhesives, dental compositions, waveguides, optical switches, colour proofing systems, colour filters, glass fibre cable coatings, screen printing stencils, resist materials, composite compositions, decolorizing materials, decolorizing materials for image recording materials, for image recording materials using microcapsules, for photographic reproductions, for encapsulating electrical and electronic components, for producing magnetic recording materials, for producing three-dimensional objects by means of stereolithography, and for producing image recording material, which comprises adding at least one photoinitiator system according to claim 1 to said monomeric, oligomeric or polymeric compounds and irradiating the resulting composition with electromagnetic radiation.

17. A coated substrate which is coated on at least one surface with a composition according to claim 8.

18. A process for the photographic production of relief images, which comprises exposing a coated substrate according to claim 17 to electromagnetic radiation either imagewise and then removing the unexposed coating composition with a solvent, or by means of a movable laser beam (without a mask) and then removing the unexposed coating composition with a solvent.

19. Compound of the formula I

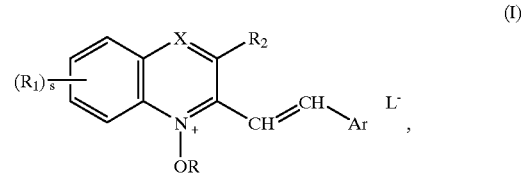

(I)

wherein

X is CH, C—$CH_3$, C—Cl, C—O—$C_1$–$C_8$alkyl or $^+$NOR $L^-$;

R is $C_1$–$C_6$alkyl, benzyl, $CH_2COOR_3$ or a group

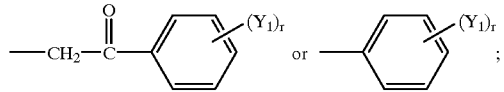

$R_1$ is $C_1$–$C_8$alkoxy, $C_1$–$C_{12}$alkyl, halogen, $NO_2$, benzyloxy or phenyloxy, wherein the phenylring in the benzyloxy or phenyloxy group is unsubstituted or substituted by $C_1$–$C_{12}$alkyl, $C_1$–$C_6$alkoxy, halogen or $CF_3$;

s is 0 to 4;

$R_2$ is hydrogen, $C_1$–$C_8$alkoxy, $C_1$–$C_{12}$alkyl, benzyloxy or phenyloxy, wherein the phenylring in the benzyloxy or phenyloxy group is unsubstituted or substituted by $C_1$–$C_{12}$alkyl, $C_1$–$C_6$alkoxy, halogen or $CF_3$;

$R_3$ is hydrogen, $C_1$–$C_{12}$alkyl or benzyl;

Ar is a group selected from (A), (B), (C), (D), (E), (F), (G), (H), (J), (K) or (L)

(A)

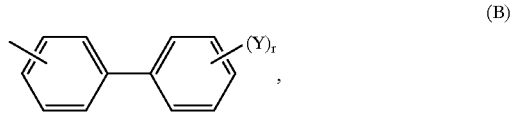

(B)

-continued (C) [structure: stilbene-type with (Y)r]

(D) [structure: naphthalene with (Y)r]

(E) [structure: anthracene with (Y)r]

(F) [structure: pyrene with (Y)r]

(G) [structure: phenanthrene with (Y)r]

(H) [structure: 5-membered heterocycle with W and (Y)r]

(J) [structure: benzofused 5-membered heterocycle with W and (Y)r]

(K) [structure: fluorene-type with W₁ and (Y)r]

(L) [structure: triphenylamine];

Y is unsubstituted or $C_1$–$C_6$alkoxy-substituted $C_1$–$C_6$alkyl, or Y is $C_1$–$C_6$alkoxy, halogen, $CF_3$, $NO_2$, $CF_3O$, benzyloxy or phenyloxy, wherein the phenylring in the benzyloxy or phenyloxy group is unsubstituted or substituted by $C_1$–$C_{12}$alkyl, $C_1$–$C_6$alkoxy, halogen or $CF_3$ or, if r is two or more and two Y are alkoxy these alkoxy groups may form a dioxolane or dioxane fused to the aryl of the arylstyryl residue;

$Y_1$ is unsubstituted or $C_1$–$C_6$alkoxy-substituted $C_1$–$C_6$alkyl, or Y is $C_1$–$C_6$alkoxy, halogen, $CF_3$, $NO_2$, $CF_3O$, benzyloxy or phenyloxy, wherein the phenylring in the benzyloxy or phenyloxy group is unsubstituted or substituted by $C_1$–$C_{12}$alkyl, $C_1$–$C_6$alkoxy, halogen or $CF_3$;

W is O, S or $CH_2$;

$W_1$ is O, S, $C(R_4)_2$ or CO;

$R_4$ is hydrogen, $C_1$–$C_8$alkoxy, $C_1$–$C_{12}$alkyl, benzyloxy or phenyloxy, wherein the phenylring in the benzyloxy or phenyloxy group is unsubstituted or substituted by $C_1$–$C_{12}$alkyl or $C_1$–$C_6$alkoxy;

r in the formula (A) and the groups

[structure: —CH₂—C(=O)—phenyl—(Y₁)r  and  —phenyl—(Y₁)r]

is 0 to 5, in the formulae (B), (C), (E), (F) and (G) is 0 to 9, in the formula (D) is 0 to 7, in the formula (H) is 0 to 3, in the formula (J) is 0 to 5 and in the formula (K) is 0 to 7; with the proviso, that, if Ar is a group (A), R is $C_1$–$C_6$alkyl, benzyl, $CH_2COOR_3$ or a group

[structure: —CH₂—C(=O)—phenyl—(Y₁)r]

and X is not $^+$NOR L$^-$, r is 2 to 5; and

L is an anion.

20. A process for the preparation of the compound of the formula I by the steps:
(1) providing an aromatic nitrogen-heterocycle having a methylene group in one or more of the 2-, 4- and 6-positions relative to a ring nitrogen;
(2) oxidising the relevant ring nitrogen to amine oxide;
(3) reacting the amine oxide with a benzaldehyde optionally carrying r substituents Y, catalysed by alkali;
(4) alkylating the product of (3) by the action of an alkylating agent such as methyl tolyl-4-sulphonate to give the oxide cation as the salt of the anion of the alkylating agent.

21. A compound of the formula X $$R_{40}\text{—}B^-(R_{40})(R_{40})\text{—}R_{41}\ G^+, \quad (X)$$

wherein $R_{40}$ is phenyl which is unsubstituted or substituted 1–5 times by halogen, $C_1$–$C_4$alkoxy, $C_1$–$C_{20}$alkyl or $C_1$–$C_{20}$haloalkyl;

$R_{41}$ is $C_3$–$C_{12}$cycloalkyl, which may be condensed with one or more aromatic rings; and G is a radical which is able to form positive ions; provided that (a) if $R_{41}$ is $C_3$–$C_6$cycloalkyl, $R_{40}$ is not unsubstituted phenyl or phenyl mono-substituted in the para-position; and (b) if $R_{40}$ is unsubstituted phenyl, $R_{41}$ is not substituted 1-acenaphthenyl.

* * * * *